(12) United States Patent
Wright et al.

(10) Patent No.: US 8,100,838 B2
(45) Date of Patent: Jan. 24, 2012

(54) VARIABLE STIFFNESS GUIDEWIRE SYSTEMS

(75) Inventors: Jay Ralph Wright, Temecula, CA (US); Sam Seunghae Ahn, Dallas, TX (US)

(73) Assignee: Wright-Ahn Technolgies, LLC, Los Angeles, CA (US)

(*) Notice: Subject to any disclaimer, the term of this patent is extended or adjusted under 35 U.S.C. 154(b) by 479 days.

(21) Appl. No.: 12/192,946

(22) Filed: Aug. 15, 2008

(65) Prior Publication Data

US 2009/0131911 A1 May 21, 2009

Related U.S. Application Data

(60) Provisional application No. 61/003,404, filed on Nov. 15, 2007, provisional application No. 61/005,745, filed on Dec. 7, 2007.

(51) Int. Cl.
*A61B 5/00* (2006.01)
*A61M 25/00* (2006.01)

(52) U.S. Cl. ................................. 600/585
(58) Field of Classification Search ........... 24/30.5, 24/327; 600/102, 585; 604/95.01, 524, 525, 604/526

See application file for complete search history.

(56) References Cited

U.S. PATENT DOCUMENTS

| | | | |
|---|---|---|---|
| 777,171 A * | 12/1904 | Engle | 198/370.05 |
| 777,191 A * | 12/1904 | Engle | 24/108 |
| 3,521,620 A * | 7/1970 | Cook | 600/585 |
| 3,600,014 A * | 8/1971 | Harris | 403/277 |
| 4,215,703 A * | 8/1980 | Willson | 600/585 |
| 4,456,017 A * | 6/1984 | Miles | 600/585 |
| 5,605,162 A | 2/1997 | Mirzaee et al. | |
| 5,762,615 A * | 6/1998 | Weier | 600/585 |
| 5,772,609 A | 6/1998 | Nguyen et al. | |
| 5,800,421 A | 9/1998 | Lemelson | |
| 5,845,646 A | 12/1998 | Lemelson | |
| 5,931,819 A | 8/1999 | Fariabi | |
| 5,957,903 A | 9/1999 | Mirzaee et al. | |
| 6,058,323 A | 5/2000 | Lemelson | |
| 6,090,139 A | 7/2000 | Lemelson | |
| 6,096,023 A | 8/2000 | Lemelson | |
| 6,139,511 A | 10/2000 | Huter et al. | |
| 6,233,474 B1 | 5/2001 | Lemelson | |

(Continued)

FOREIGN PATENT DOCUMENTS

WO 2004002310 A1 1/2004

OTHER PUBLICATIONS

Office Action in U.S. Appl. No. 12/192,950, dated Feb. 24, 2011.

*Primary Examiner* — Max Hindenburg
*Assistant Examiner* — Charles Becker
(74) *Attorney, Agent, or Firm* — Nixon Peabody LLP

(57) ABSTRACT

A variable-stiffness guidewire system which comprises an elongated flexible guidewire. The guidewire has a body and a guidewire head coupled to the body. The guidewire head is slidably moveable with respect to a guidewire collar of the body to adjust a stiffness of the guidewire. A tool is utilized with the guidewire to engage the guidewire head and move the guidewire head a desired distance from the guidewire collar to achieve a desired stiffness. The tool has a first mechanism that is configured to selectively deploy an insert to be positioned between the guidewire head and the guidewire collar. The insert maintains the desired stiffness of the guidewire.

17 Claims, 16 Drawing Sheets

U.S. PATENT DOCUMENTS

| | | |
|---|---|---|
| 6,286,514 B1 | 9/2001 | Lemelson |
| 6,287,292 B1 | 9/2001 | Fariabi |
| 6,287,294 B1 | 9/2001 | Lemelson |
| 6,293,282 B1 | 9/2001 | Lemelson |
| 6,321,106 B1 | 11/2001 | Lemelson |
| 6,327,492 B1 | 12/2001 | Lemelson |
| 6,394,997 B1 | 5/2002 | Lemelson |
| 6,400,980 B1 | 6/2002 | Lemelson |
| 6,401,988 B1 * | 6/2002 | Parent et al. .......... 222/326 |
| 6,468,203 B2 | 10/2002 | Belson |
| 6,491,663 B1 | 12/2002 | Lemelson |
| 6,514,237 B1 | 2/2003 | Maseda |
| 6,524,301 B1 | 2/2003 | Wilson et al. |
| 6,532,387 B1 | 3/2003 | Marchitto et al. |
| 6,562,021 B1 | 5/2003 | Derbin et al. |
| 6,610,007 B2 | 8/2003 | Belson et al. |
| 6,632,215 B1 | 10/2003 | Lemelson |
| 6,638,266 B2 | 10/2003 | Wilson et al. |
| 6,679,836 B2 | 1/2004 | Couvillon, Jr. |
| 6,770,027 B2 | 8/2004 | Banik et al. |
| 6,869,396 B2 | 3/2005 | Belson |
| 6,890,297 B2 | 5/2005 | Belson |
| 6,969,395 B2 | 11/2005 | Eskuri |
| 7,020,516 B2 | 3/2006 | Flock et al. |
| 7,044,907 B2 | 5/2006 | Belson |
| 2003/0065373 A1 | 4/2003 | Lovett et al. |
| 2006/0047303 A1 | 3/2006 | Ortiz et al. |
| 2009/0254001 A1 | 10/2009 | Wright et al. |
| 2010/0249656 A1 | 9/2010 | Wright et al. |

* cited by examiner

VARIABLE STIFFNESS GUIDEWIRE SYSTEMS

STATEMENT OF RELATED APPLICATIONS

The present application claims the benefit of priority based on U.S. Provisional Patent Application Ser. No. 61/005,745, filed on Dec. 7, 2007, and Provisional Patent Application Ser. No. 61/003,404, filed on Nov. 15, 2007, both in the name of inventors Jay Wright and Samuel Ahn, and entitled "Variable Stiffness Guidewire Systems."

TECHNICAL FIELD

The present disclosure relates generally to variable stiffness guidewire systems.

BACKGROUND

FIG. 1 illustrates an example of an existing variable stiffness guidewire system. As shown in FIG. 1, the guidewire 10 is shown inside the aorta A of a patient, wherein the guidewire 10 is shown inserted through a proximal opening of a catheter hub 12 of a catheter 14 and extending out of a distal opening or lumen 16 of the catheter 14. The guidewire 10 shown in FIG. 1 has the ability to obtain variable stiffness to allow it to travel through different arterial branches and also be stable such that the weight of the catheter 14 and/or other instruments (e.g. balloon catheter, sensors) or drugs may be delivered to the desired location of the patient during a medical procedure. The stiffness of the guidewire 10 is variably adjusted at the proximal end by the physician by pulling a head (not shown) of the guidewire away a desired distance from the coil body 18 of the guidewire. However, the head of the guidewire 10 is small in diameter such that pulling the head away from the coil body 18 usually requires the assistance of a tool 20.

As shown in FIG. 1, the tool 20 is significantly larger than the guidewire 10 which allows the user to comfortably manipulate the tool 20 and guidewire 10. However, this configuration of guidewire 10 and tool 20 is disadvantageous considering that the tool 20 is relatively larger in diameter than that of the guidewire 10. Thus, the relatively larger tool 20 does not allow loading and/or unloading of other components over the catheter 14 at its proximal end 12 without first removing the tool 20 from the guidewire 10. Removing the tool 20 may cause the loss of tension between the head and coil body of guidewire 10, thereby effectively causing loss in the desired stiffness and stability in the guidewire to deliver the instruments or drugs to the desired location within the patient.

Accordingly, a need exists for a variable stiffness guidewire system and tool which allows adjusting of the guidewire stiffness as well as maintaining that stiffness to allow loading and unloading of instruments or drugs to the desired location within the patient without losing or compromising the maintained stiffness in the guidewire.

OVERVIEW

Systems for the flexible catheterization of arterial branches by the percutaneous entry techniques and, more particularly, such systems provide a variable stiffness guidewire for advancement into the lumens of branched arteries, vessels and cavities remote from the point of entry of the catheter. The systems include removable devices for selectively maintaining guidewire stiffness by maintaining tension after removal of the actuator, or tool. Further, the system includes a mechanism for selectively inserting the removable devices on the tensioned end of the guidewire.

In an embodiment, a variable-stiffness guidewire system comprises an elongated flexible guidewire. The guidewire has a body and a guidewire head that is coupled to the body. The guidewire head is slidably moveable with respect to a guidewire collar of the body to be able to adjust a stiffness of the guidewire. A tool is utilized with the guidewire and is configured to engage the guidewire head and move the guidewire head a desired distance from the guidewire collar to achieve a desired stiffness. The tool has a first mechanism that is configured to selectively deploy an insert to be positioned between the guidewire head and the guidewire collar, wherein the insert maintains the desired stiffness of the guidewire.

In an embodiment, the insert remains between the guidewire head and the guidewire collar and maintains stiffness of the guidewire after the tool disengages the guidewire. In an embodiment, the tool further comprises a second mechanism that is coupled to the tool. The second mechanism is configured to selectively remove the insert from between the guidewire head and the guidewire collar. In an embodiment, the insert has a cross-sectional dimension that is smaller than or substantially equal to a diameter of the body of the guidewire. In an embodiment, the tool further comprises an engaging mechanism that includes a tension brace and a collar interface. The tension brace is configured to engage the guidewire head and the collar interface is configured to abut the guidewire collar. The tension brace is actuatable between a retracted position and an extended position with respect to the collar interface, wherein the insert is positioned between the guidewire head and the guidewire collar when the tension brace is in the extended position. In an embodiment, the guidewire head is triangular in shape, whereby the tool further comprises an engaging mechanism configured to engage the guidewire head. The engaging mechanism includes a first triangular-shaped engaging aperture that extends from a first surface to a second surface of the tension brace. The first aperture is positioned in a first orientation to allow the triangular guidewire head to pass from the first surface to the second surface when the triangular guidewire head is aligned with the first orientation of the first engaging aperture. The engaging mechanism includes a second triangular-shaped engaging aperture that extends from the second surface only partially toward the first surface of the tension brace. The second aperture is positioned in a second orientation at an angle with respect to the first orientation of the first aperture, wherein the second aperture is configured to engage the triangular guidewire head when the triangular guidewire head is aligned with the second orientation of the first engaging aperture.

A tool for use with a variable-stiffness guidewire having a guidewire head and a guidewire collar. The tool comprises a body; an engaging mechanism is coupled to the body and is adapted to engage a guidewire head of a guidewire. An actuator is coupled to body and configured to move the engaging mechanism and the guidewire head away from a guidewire collar a first distance to achieve a first stiffness of at least a portion of the guidewire. A mechanism is coupled to the body and is configured to selectively remove an insert coupled to the guidewire and having a length dimension substantially equal to the first distance positioned between the guidewire head and the guidewire collar to maintain the first stiffness in the at least a portion of the guidewire.

In an embodiment, the insert mechanism is configured to selectively deploy the insert to be positioned between the guidewire head and the guidewire collar to achieve the first stiffness. In an embodiment, the engaging mechanism is configured to move the guidewire head back toward the guidewire collar after the insert is removed to decrease the first stiffness of the guidewire. In an embodiment, the engaging mechanism is configured to move the guidewire a second distance with respect to the guidewire collar after the insert is removed to achieve a second stiffness in the guidewire. The insert mechanism is configured to selectively deploy a second insert having a length dimension substantially equal to the second distance to maintain the second stiffness. In an embodiment, the mechanism itself is selectively removeable from the body of the tool.

In an embodiment, a tool for use with a variable-stiffness guidewire which has a guidewire head and a guidewire collar. The tool comprises a body. An engaging mechanism is coupled to the body and is adapted to engage a guidewire head of a guidewire. An actuator is coupled to body and is configured to move the engaging mechanism and the guidewire head away from a guidewire collar a first distance to achieve a first stiffness of at least a portion of the guidewire. A mechanism is coupled to the body and is configured to selectively deploy an insert having a length dimension substantially equal to the first distance between the guidewire head and the guidewire collar, wherein the insert maintains the first stiffness in at least a portion of the guidewire.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

In the drawings.

DETAILED DESCRIPTION

Example embodiments are described herein in the context of a variable stiffness guidewire system. Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same reference indicators will be used throughout the drawings and the following description to refer to the same or like items.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In general, a variable stiffness surgical guidewire system for use with a flexible catheter, the system includes an elongated flexible guidewire and an actuator (also referred to as tool) selectively coupleable to the proximal end of the flexible guidewire for selectively controlling the stiffness of, at least, sections thereof. The system can be used in, for example, medical techniques for treating systems including vascular, urinary, genital, gastro-intestinal, respiratory, biliary, and neurological systems. Preferably, the system may also include a removable device to selectively maintain guidewire stiffness by maintaining tension after removal of the tool.

Figure 1:
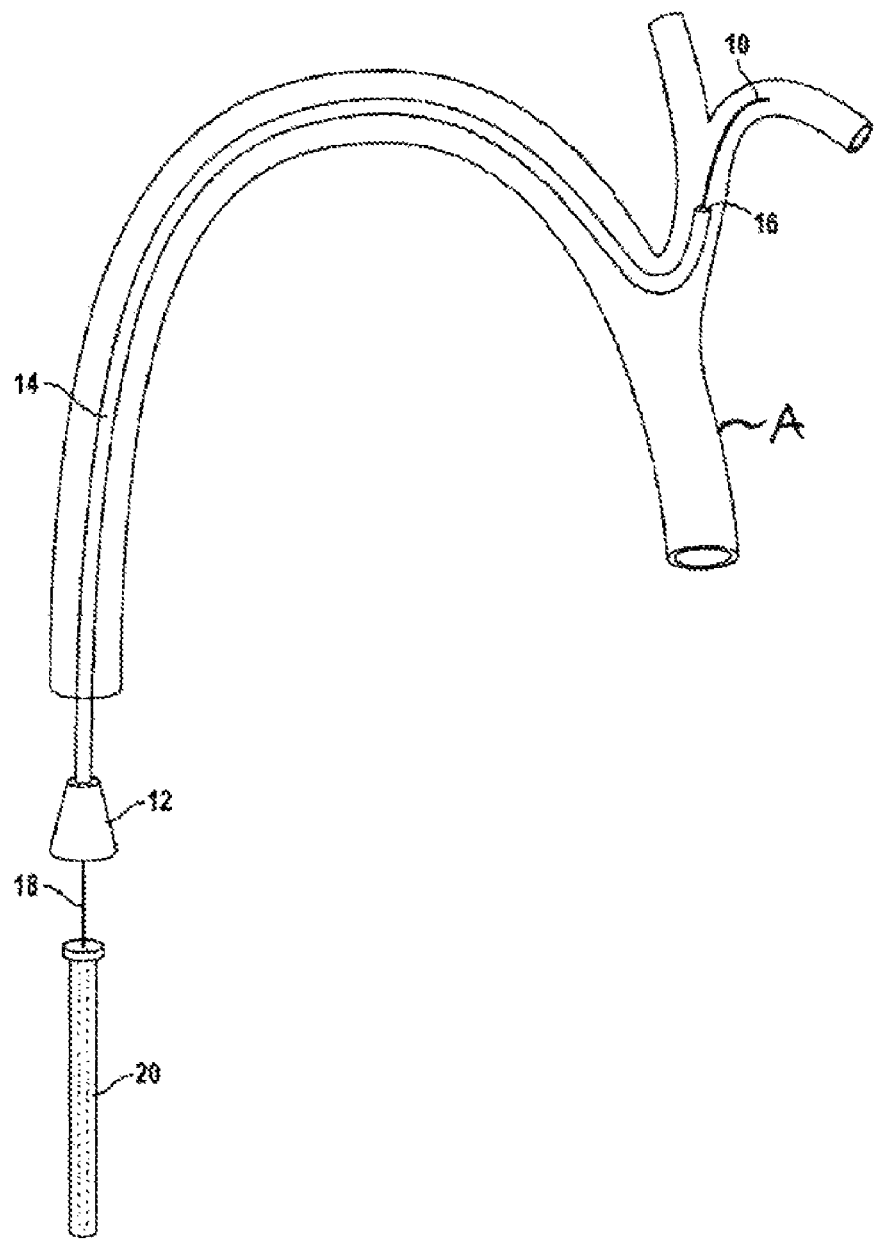
FIG. 1 illustrates a variable stiffness guidewire in accordance with the prior art.
Figure 2A:
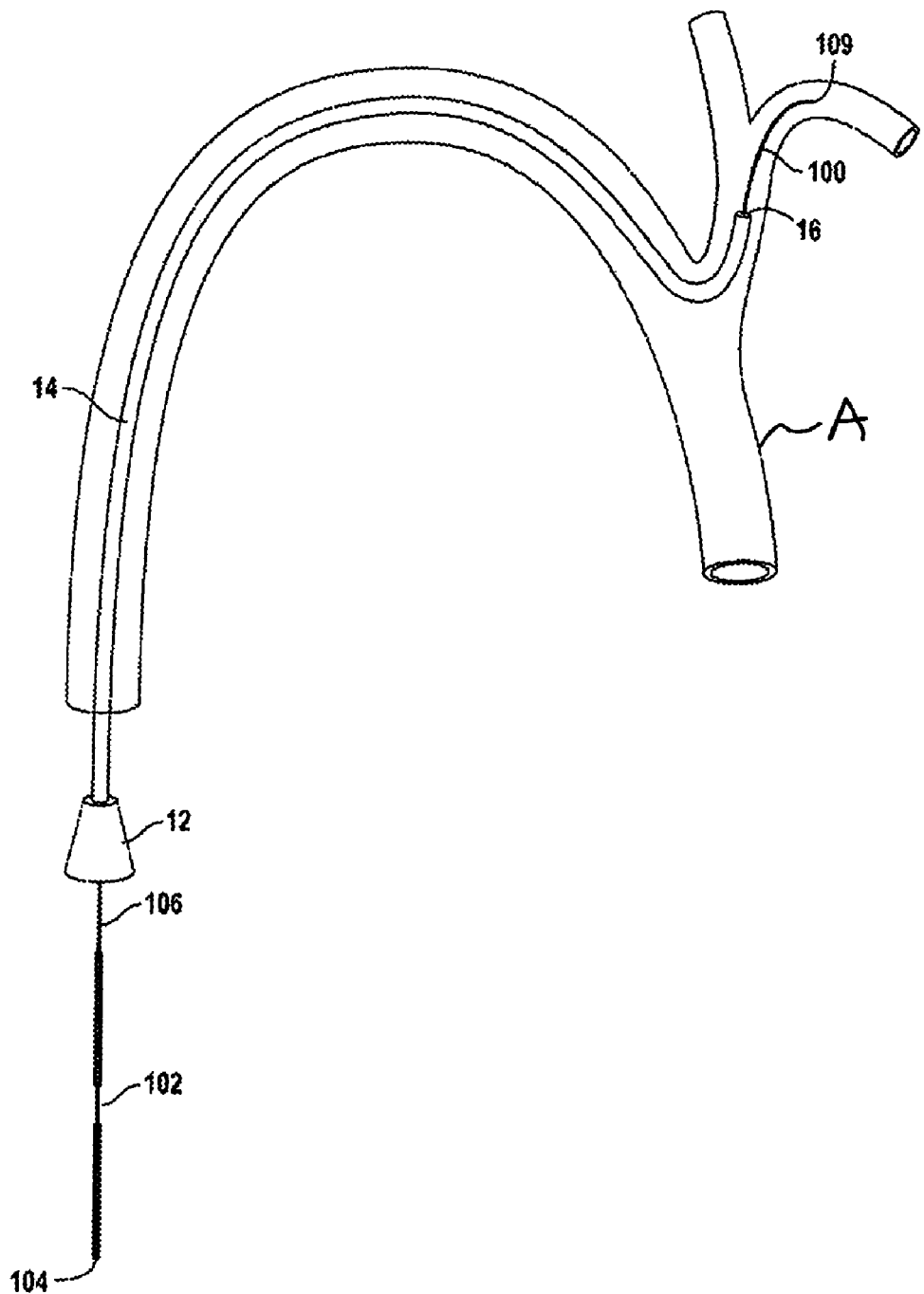
FIG. 2A illustrates a variable stiffness guidewire in accordance with an embodiment.

FIG. 2A illustrates a guidewire 100 in accordance with an embodiment for use during a surgical procedure. As shown in FIG. 2A, the guidewire 100 is shown inside the aorta A of a patient, wherein the guidewire 100 is inserted through a proximal opening 12 of a catheter 14 and extends out of a distal opening or lumen 16 of the catheter 14. In contrast to the guidewire 10 in FIG. 1, the guidewire 100 in FIG. 2A includes a tension wire 102 at its proximal end as well as tension head 104 which is exposed and may be manipulated by the user.

The tension head 104 is movable with respect to the body 106 of the guidewire 102. The guidewire 100 has a variable stiffness feature in which the stiffness of the guidewire 100 varies proportionally with the distance between the tension head 104 and the coil body 106. Therefore, in operation, the stiffness a portion or all of the guidewire 100 will increase as the tension head 104 is moved away from the body 106. In contrast, movement of the tension head 104 in the opposite direction (toward the body 106) will cause the stiffness of the guidewire 100 to decrease. Maintaining the position of the tension head 104 with respect to the body 106 at a particular position will maintain the stiffness of the guidewire body 106. In particular, the construction of the guidewire 100, as will be discussed in more detail below, allows the distal end of the guidewire 100 to remain stationary while the stiffness of the guidewire is increased.

Figure 2B:
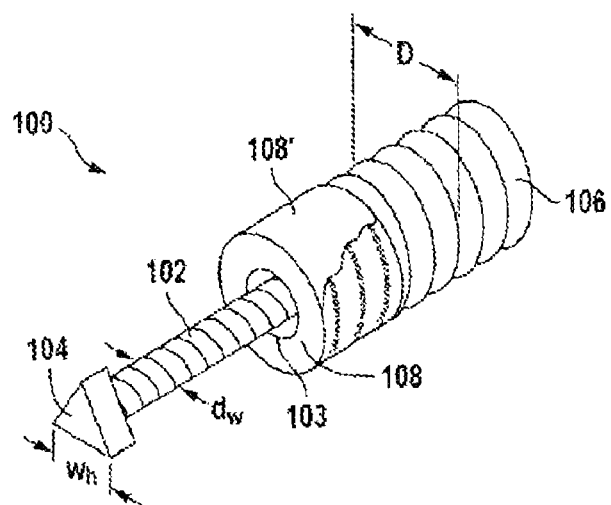
FIG. 2B illustrates a perspective view of the proximal end of the guidewire body in accordance with an embodiment.

FIG. 2B illustrates a perspective view of the proximal end of the guidewire 100 in accordance with an embodiment. As shown in FIG. 2B, the guidewire 100 includes a coil body 106, a tension wire 102 coupled to the body 106 extendable out of the body 106, and a tension head 104 coupled to the tension wire 102. In addition, the guidewire 100 is shown in FIG. 2B to preferably have a collar 108' which represents a portion of the end of the coil body 104 that is closest to the tension head 104.

In an embodiment, the collar 108' is formed by soldering and metal flowing together 3-5 windings of the coil at the proximal end of the coil body wire 106. Thereafter, it is preferred that the soldered area is grounded and smoothed to create a smooth outer circular body with a flat collar end 108 which is perpendicular to the outer surface 108 of the collar in accordance with an embodiment. The guidewire 100 benefits from construction of the collar 108' as the collar 108' serves to increase the structural stability as well as the ability to bear tension (and resulting increased stiffness) enabled by soldering the end coils together. The collar 108' also serves as a retaining wall which allows the windings of the guidewire to contract and press against one another when the stiffness of the guidewire 100 is increased. It should be noted that soldering and metal flowing is one example of creating the collar 108' and that any other appropriate method is contemplated. It is also contemplated that the guidewire 100 not use a collar 108' but some other member which serves the functions of a retaining wall that allows the coil windings of the guidewire 100 to contract press together when an increase in stiffness of the guidewire 100 is desired.

Figure 2C:
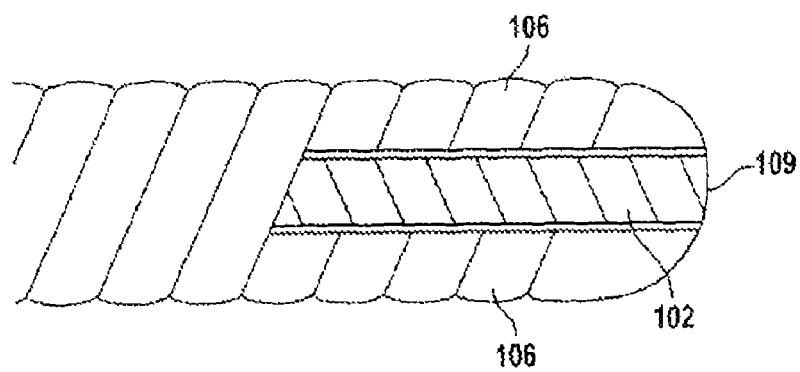
FIG. 2C illustrates a side view of the distal end of the guidewire body in accordance with an embodiment.
Figure 2D:
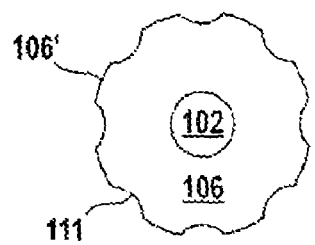
FIG. 2D illustrates an end view of the distal end of the guidewire body in accordance with an embodiment.

FIG. 2C illustrates a side view of the distal end of the guidewire body in accordance with an embodiment. FIG. 2D illustrates an end view of the distal end of the guidewire body in accordance with an embodiment. As shown in FIGS. 2B and 2C, the tension wire 102 preferably is comprised of one or more wires which are wound together to form a coiled or cable type body, whereby the coils of the tension wire 102 are opposite to the coils of the outer body 106. The tension wire 102 has a proximal end and a distal end, whereby the proximal end of the wire 102 is attached to the tension head 104 as shown in FIG. 2B. In an embodiment, the tension head 104 is separately manufactured from the tension wire 102 such that both components are coupled to one another. In an embodiment, the tension wire 102 is formed with the tension head 104 being integrally formed therewith.

The distal end of the tension wire 102 is attached to the distal end 109 of the body 106 of the guidewire 100. As shown in FIGS. 2C and 2D, the distal end of the wire 102 is positioned at the distal end 109' of the guidewire 100, whereby the outer body 106 is preferably crimped to securely mount the tension wire 102 to the outer body 106. In particular, as shown in FIG. 2D, the crimped areas 111 force the body 106 to apply a frictional force onto the tension wire 102, thereby allowing the wire 102 and the body 106 to withstand more tension force during stiffening of the guidewire 100 than previous soldering methods. Once the ends of wire 102 and outer body 106 are crimped, the distal end 109 is preferably smoothed by known methods (e.g. soldering, machining) to form a smooth, rounded distal end 109 of the guidewire 100. In the embodiment shown in FIG. 2D, an 8-point micro-crimp style tool may be used to crimp the outer body 106 to the tension head 102, it should be noted that any other appropriate tool may be utilized.

As stated above, the coil windings of the tension wire 102 are opposite to that of the outer body 106 of the guidewire 100. In an embodiment, the coil windings of the outer body 106 traverse clockwise along the length of the body 106, whereas the coil windings of the tension wire 102 traverse counterclockwise along the length of the wire 102, or vice versa. The opposite windings of the two members allow the distal end of the guidewire 100 to maintain its dimensional stability while the guidewire 100 is stiffened and under tension. Additionally, the opposed windings allow the distal end of the guidewire 100 to maintain its location with respect to its proximal end while under tension. Further, the method of crimping the ends of the tension wire 102 and outer body 106 allows tension to be applied-to and released-from the guidewire 100 multiple times without crushing or damaging the outer body 106. Accordingly, the preferred design of the guidewire 100 discussed above specifically minimizes or avoids distal tip 109 deflection as well as any tendency for the distal portion of the guidewire 100 to straighten itself out with respect to the proximal end. By allowing the distal portion 109 to maintain its position while the guidewire 100 is stiffened, the user is provided the positional stability to deliver the necessary surgical instruments and/or medicine to be delivered more consistently and accurately to the desired location within the patient. It should be noted that the other figures herein depicting the guidewire 100 may not show the coiled tension wire 102 for clarity purposes.

An example of the construction for guidewire 100 is as follows: the body 106 has an outer diameter of 0.035"×0.007" of 304 sst wire×150 cm-300 cm long coil body. Additionally, 5-10 coils located at the proximal end of the outer body 106 are soldered together and polished or grounded to form the collar 108' and collar end 108. With the outer diameter of the collar 108' preferably having the same outer diameter as the outer diameter of the coil body 106, and the inner diameter 103 of the collar 108' having a slightly larger diameter than the outer diameter of the tensioning wire 102, whereby the outer body 106 moves freely over the tension wire 102. One example of an acceptable tension wire 102 has a 0.015" outer diameter 304sst monofilament tension core which provides excellent tensile strength (approximately 70 lbs.) and acceptable stiffness.

A preferred example of the tension wire 102 is a cable-braid wire which provides excellent tensional strength and stiffness and superior positional stability of the distal end of the guidewire 100 when under tension. In an embodiment, left hand or right hand wound coiled bodies of the guidewire 100 are acceptable for use with left hand or right hand twist cables or monofilament core wires. The oppositely configured outer coil body and tension wire are such that the user experiences improved torsional stability when the guidewire 100 is tensioned to a desired stiffness. This configuration may be more favorable than others for certain applications requiring, namely, additional torsional strength and dimensional stability during the procedures.

Referring back to FIG. 2B, the tension wire 102 and head 104 are shown a distance away from the collar 108 and body 106 in a default natural state. The guidewire 100 is designed such that the body 106 will increase in stiffness as the head 104 (and wire 102) is further actuated away from the collar 108. In contrast, the body 106 will decrease in stiffness as the tension head 104 (and wire 102) is moved toward the collar 108 of the body 106.

As stated, it is preferred that the head 104 is positioned a certain distance from the collar in a default nature state, whereby a portion of the wire 102 remains exposed outside the collar 108. Alternatively, the head 104 abuts the collar 108 and the wire 102 is completely within the body 106 when the guidewire 100 is in the default, natural state. For purposes of this description, it will be assumed that the head 104 is positioned a certain distance from the collar 108 and a portion of the wire 102 is exposed, as shown in FIG. 2B, when the guidewire 100 is at its default natural state.

As shown in FIG. 2A, the body 106 has a diameter D, whereby the tension wire 102 has a diameter $d_w$, and the tension head 104 has a width dimension $w_h$. The diameter $d_w$ of the tension wire 102 is preferably smaller than the diameter D of the body 106. Additionally, it is preferred that the width $w_h$ of the tension head 104 is greater than the diameter $d_w$ of the tension wire 102 but preferably smaller than the diameter D of the body 106. Considering that the inner diameter of the instrument or drug carrying catheter is slightly larger than the diameter D of the body, a smaller width dimension $w_h$ of the tension head 104 will ensure that the medical instruments and drug may be loaded or unloaded directly over the head 104 of the guidewire 100 without problems or resistance.

It should be noted that the tension head 104 is shown in FIG. 2B to have a triangular shape. Although this is a preferred shape, the tension head 104 may alternatively have any other shape including, but not limited to, square, hexagonal, pentagonal, trapezoidal, spherical, circular, etc. Considering that the head 104 is shown as triangular in the embodiment in FIG. 2A, the width dimension $w_h$ is the length of a longest side (or any side if the head 104 is an equilateral triangle). In an embodiment that the head 104 is another shape, the width dimension $w_h$ is preferably the length of the longest side of the shape.

Figure 3A:
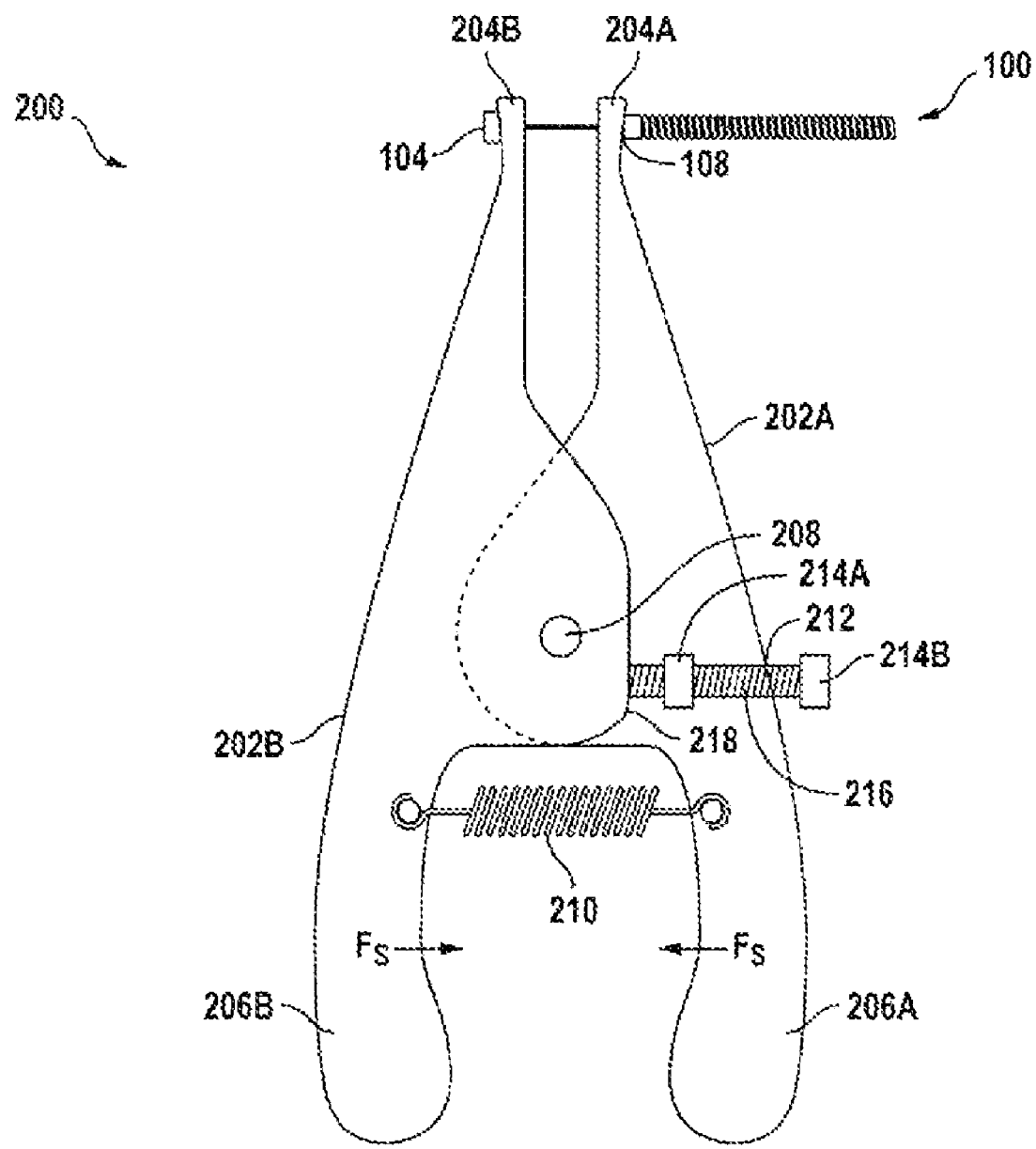
FIGS. 3A-3B illustrate diagrams of guidewire tensioning tool embodiments.

FIG. 3A illustrates a diagram of a guidewire tensioning tool in accordance with an embodiment. As shown in FIG. 3A, the tool 200 includes a body having a first portion 202A and a second portion 202B, whereby each portion has a pair of respective jaws 204A, 204B and a pair of respective handles 206A, 206B coupled to one another at a fulcrum 208. A spring-like member 210 is preferably coupled to both sides 202A, 202B. The spring-like member 210 preferably applies an inwardly directed force $F_s$ (as shown by the arrows) which urges the handles 206A, 206B to move toward each other and thereby urging the jaws 204A, 202B to move apart from one another by default. It should be noted that although a regular spring 210 is shown in the Figures of the tool 200, it is contemplated that any type of resilient material may be used in substitution to a typical spring, including but not limited to, a leaf spring, foam, elastics, etc.

The jaws 204A, 204B are configured to receive and engage the tension head 104 of the guidewire 100. In particular, controlled movement of the jaws 204A, 204B toward or away from one another will result in the corresponding stiffness or flaccidness of the guidewire body 106. As will be discussed, the jaw 204B preferably includes a guidewire engagement feature which allows the jaw to engage the tension head 104 during operation. Some example embodiments of the guidewire engagement feature will now be described in FIGS. 4A-4D.

Figure 4A:
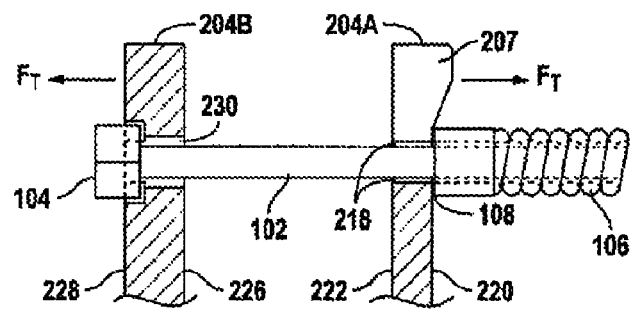
FIGS. 4A-4D illustrate detailed views of the guidewire engagement mechanism in accordance with embodiments.

FIG. 4A illustrates a detailed view of the guidewire engagement feature in accordance with an embodiment. As shown in FIG. 4A, the tool 200 has jaws 204A and 204B, whereby jaw 204A will be referred to as the distal jaw 204A and jaw 204B will be referred to as the proximal jaw 204B. The distal jaw 204A shown in FIG. 4A has an open fork aperture 218 which allows the wire 102 to vertically slip downward into the aperture 218 from the top surface of the jaw 204A. In an embodiment, the jaw 204A has a flanged portion 207 is maintains the position of the collar 108 and prevents it from moving vertically upward the top surface of the jaw 204A and disengaging from the jaw 204A. The aperture's 218 cross-sectional dimension is preferably smaller than the diameter of the collar 108 such that the collar 108 remains to the outside surface 220 of the distal jaw 204A. In an embodiment, the cross sectional dimension of the aperture 218 is constant from the outside surface 220 to the inside surface 222 of the distal jaw 204A. In an embodiment, as shown in FIG. 4D, the cross sectional dimension of the aperture 218 is not constant from the outside surface 220 to the inside surface 222, but instead has a recessed portion 224 which allows the collar to sit within a portion of the distal jaw 204A. In an embodiment, the aperture 218 has a tapered shape in which the size of the aperture is larger near the outside surface 220 than the inside surface 222.

Figure 4B:
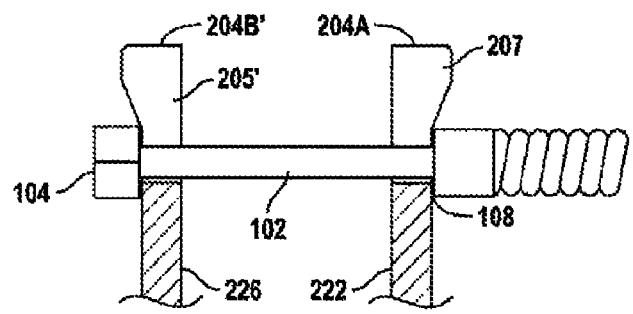
Figure 4C:
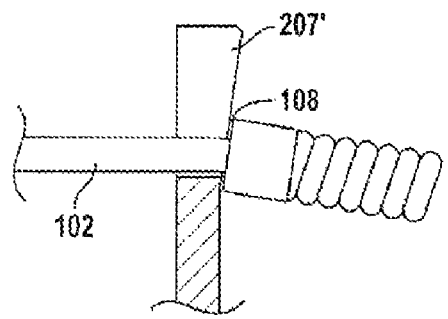
Figure 4D:
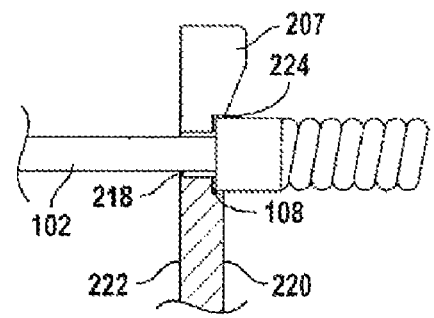

FIGS. 4B and 4C illustrate different types of jaw configurations. In FIG. 4B, the proximal jaw 204B has a open-ended fork arrangement, such as a pliers beak, as with the distal jaw 204A. The flange 205' of the proximal jaw 204B prevents the head 104 from vertically running upward and disengaging from the jaw 204B. FIG. 4C illustrates the distal jaw having a tapered flange 207' design which also maintains the collar 108 again the outer surface of the jaw 204A.

Additionally, the proximal jaw 204B preferably includes an engaging aperture 230 therethrough which has a cross-sectional dimension large enough to allow the tension head 104 to extend through, whereby the tension head 104 engages the outer surface 228 when inserted through the engaging aperture 230 from the inner surface 226 to the outer surface 228. However, once the tension head 104 passes through the engaging aperture 230, the aperture 230 is selectively engaged with the tool 220, whereby the head 104 is unable to pass through the aperture 230 back toward the collar body 108 until desired by the user.

Figure 5A:
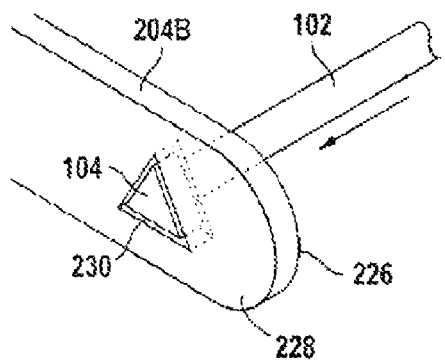
FIGS. 5A-5C illustrates perspective views of the guidewire engaging feature of the tool in accordance with embodiments.
Figure 5B:
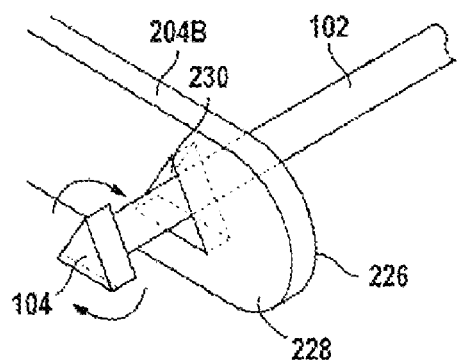
Figure 5C:
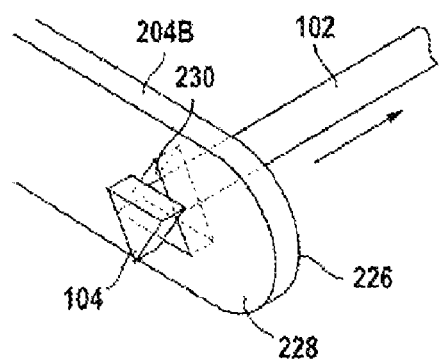

FIGS. 5A-5C illustrates perspective views of the guidewire engaging feature of the tool 200 in accordance with an embodiment. It should be noted that although the engaging feature is described within the context of the tool 200, the engaging feature may be incorporated in any other of other devices described herein (e.g. tools 1200, 1400, 1500 discussed below). As stated above, the tension head 104 preferably has a triangular shape in an embodiment. Similarly, in an embodiment, the engaging aperture 230 has a similar triangular shaped passage through the entire thickness of the proximal jaw 204B and/or the distal jaw 204A, as shown by the phantom lines in FIG. 5A. In FIG. 5A, the triangular head 104 is shown passing through the aperture 230 from the inner surface 226 to the outer surface 228 of the jaw 204B, whereby the shape of the head 104 is in communication and registers with the corresponding shape of the aperture 230. As such, the dimensions of the aperture 230 are at least slightly larger than the dimensions of the head 104 to allow the head 104 to traverse through the aperture 230. In FIG. 5B, the head 104 traverses entirely through the aperture 230 and is rotated about axis A, as shown by the arrows, to allow the head 104 to be engaged with a tool 200, 1200 as discussed below. In an embodiment, the head 104 does not rotate, but instead the jaw 204B is rotated to bring the combination to the configuration in FIG. 5C.

In FIG. 5C, the head 104 is rotated 60 degrees out of alignment with the aperture 230, whereby the head 104 is then urged into frictional contact with the outer surface 228 of the jaw 204B by the guidewire body 106. By being in frictional contact with the outer surface 228 of the jaw 204B, the head 104 is thereby engaged and in a locked position with the jaw 204B. To unlock and disengage the head 104 from the tool 200, the head 104 is rotated 60 degrees about axis A until it is aligned with the aperture 230, as shown in FIG. 5A.

Figure 6A:
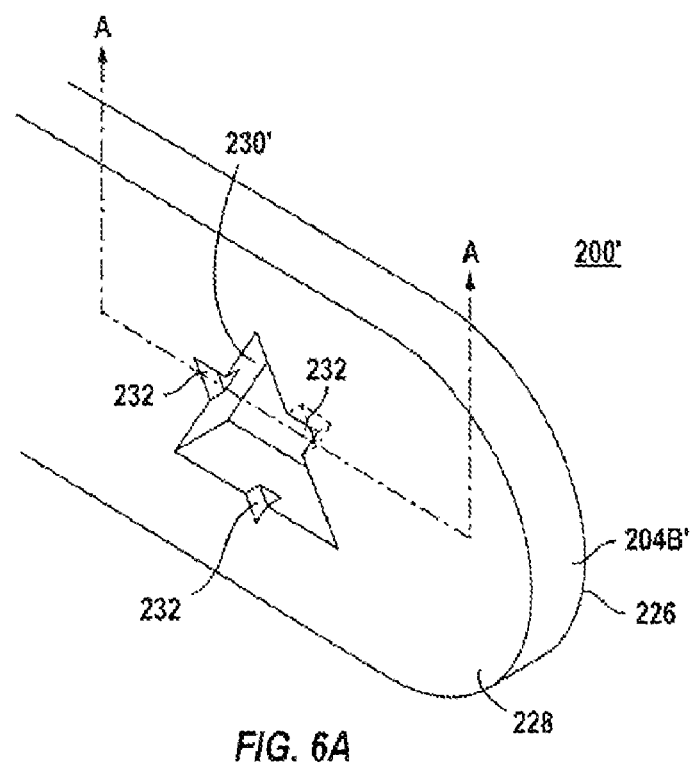
FIG. 6A illustrates a perspective view of the guidewire engaging feature of the tool 200 in accordance with an embodiment.
Figure 6B:
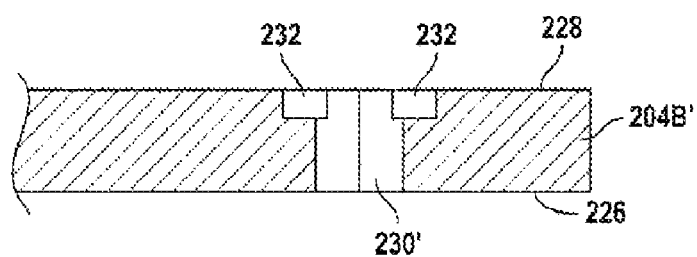
FIG. 6B illustrates a cross sectional view of the aperture of FIG. 6A along section B-B in accordance with an embodiment.

FIG. 6A illustrates a perspective view of the guidewire engaging feature of the tool 200 in accordance with an embodiment. It should be noted that although the engaging feature is described within the context of the tool 200, the engaging feature may be incorporated in any of the other devices described herein (e.g. tools 1200, 1400, 1500). In an embodiment, the aperture 230' includes a recessed portion 232 which is 60 degrees out of alignment with the aperture 230' such that the head 104 is securely seated within the recessed portion 232 when in the locked and engaged position. The recessed portion 232 secures the head 104 and prevents the head 104 from unintentionally rotating when engaged by the jaw 204B' or any of the other devices described herein (e.g. tools 1200, 1400, 1500). FIG. 6B illustrates a cross sectional view of the aperture 230' along section B-B in accordance with an embodiment.

Figure 6C:
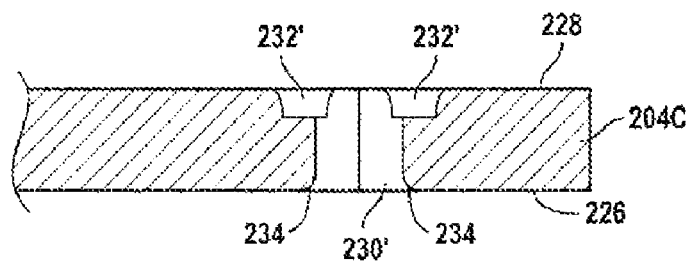
FIG. 6C illustrates an alternate cross sectional view of the aperture of FIG. 6A along section C-C in accordance with an embodiment.

FIG. 6C illustrates an alternate cross sectional view of the aperture 232' in which the recess tapers outward toward the outer surface 230'. In the embodiment in FIG. 6C, the rounded tapered shaped recess 232' facilitates easier interfacing and engaging as well as disengaging of the triangular head 104 from the aperture 232'.

Figure 3B:
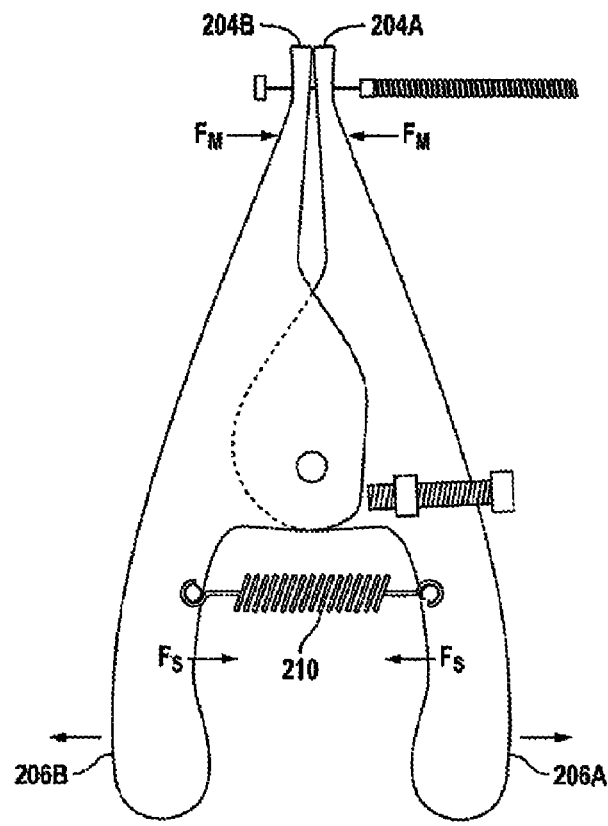

Once the head 104 is engaged and in a locked position with the tool 200, the guidewire 100 is then able to be manipulated using the tool. Referring back to the tool embodiment shown in FIG. 3A, the tool 200 includes a stiffness adjustment mechanism 212 which serves to provide an equal and opposing force to the spring 210 to stabilize mechanical movement of the jaws 204A, 204B. The embodiment of the adjustment mechanism 212 shown in FIG. 3A comprises a nut 216 and one or more bolts 214A, 214B which are coupled to the tool 200 in the embodiment shown in FIG. 3A. The adjustment mechanism 212 operates by rotation of one or both of the nuts 214A, 214B in predetermined directions which thereby causes the bolt 216 to move transversely in the desired direction (as shown by the arrow). For example, rotation of the nut 214A and/or 214B in a predetermined direction will cause the nut 216 to move toward the fulcrum 208 and eventually abuts the middle body 218 of the tool 200. Considering that the spring like member 210 urges the handles 206A, 206B toward one another (and thus the jaws 204A, 204B away from each other), the bolt 216, upon applying a counter force to the middle body 218, will cause handles 206A and 206B to move away from one another and ultimately force the jaws 204A, 204B of the tool to move closer to one another. Considering that the stiffness of the engaged guidewire 100 increases as the jaws 204A, 204B are moved apart from one another, the adjustment mechanism 212, by default or when not in use, presses against the middle body 218 and causes the handles 206A, 206B to be apart from one another a maximum allowable distance. This allows the tool 200 to allow easy manipulation of the guidewire 100. FIG. 3B illustrates the preferred default position of the tool 200 in accordance with an embodiment.

Figure 10:
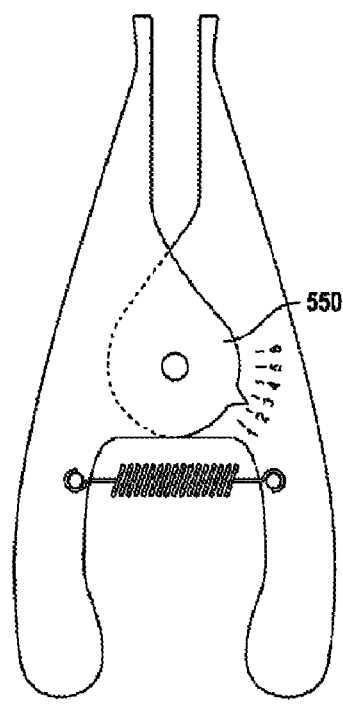

In operation, upon the head 104 of the guidewire 100 being engaged by the tool 200, the user is able to manipulate the adjustment mechanism 212 by pressing the handles 206A, 206B toward each other and thereby moving the jaws 204A, 204B away from one another. The gradual movement of the jaw 204B away from jaw 204A forces the tension head 104 away from the collar 108 and thus gradually increases the stiffness of the guidewire 100 to a desired amount. In an embodiment, the tool 200 may include a caliper type measuring feature which allows the user to know the amount of stiffness the guidewire 100 is undergoing based on the measured distance between the jaws 204A, 204B (FIG. 10).

Figure 7:
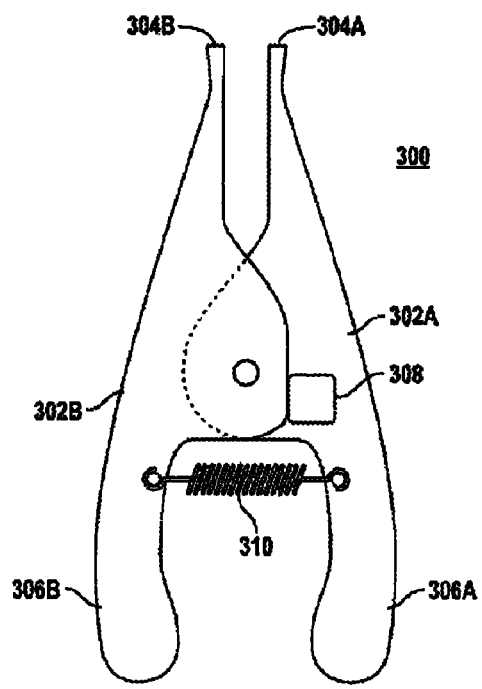
FIGS. 7-10 illustrate diagrams of tools in accordance with different embodiments.

FIG. 7 illustrates a diagram of a tool in accordance with an embodiment. As shown in FIG. 7, the tool 300 is similar in design and operation to the tool 200 described in FIGS. 3A and 3B. In contrast to the tool 200, the tool 300 includes a hard stop mechanism 308 configured to provide one or more fixed stops, whereby each stop represents a predetermined distance between jaws 304A and 304B. The stop 308 shown in FIG. 7 is preferably fixed and defines the maximum distance (and thus maximum stiffness in the guidewire 100) which jaws 304A, 304B may be apart from one another when the tension head 104 is engaged thereto. In operation, middle body 318 is shaped such that it comes into contact with the stop 308 and thus does not allow handles 302A, 302B to be pressed toward one another any further. In operation, the hard stop mechanism 308 allows the guidewire 100 to achieve three levels of stiffness: soft or no stiffness when the guidewire 100 is not engaged to the tool 300, intermediate stiffness when the guidewire 100 is engaged to the tool 300 but the handles 302A, 302B are not pressed together, and maximum stiffness when the guidewire 100 is engaged to the tool 300 and the middle body 318 is pressing against the hard stop 308.

Figure 8:
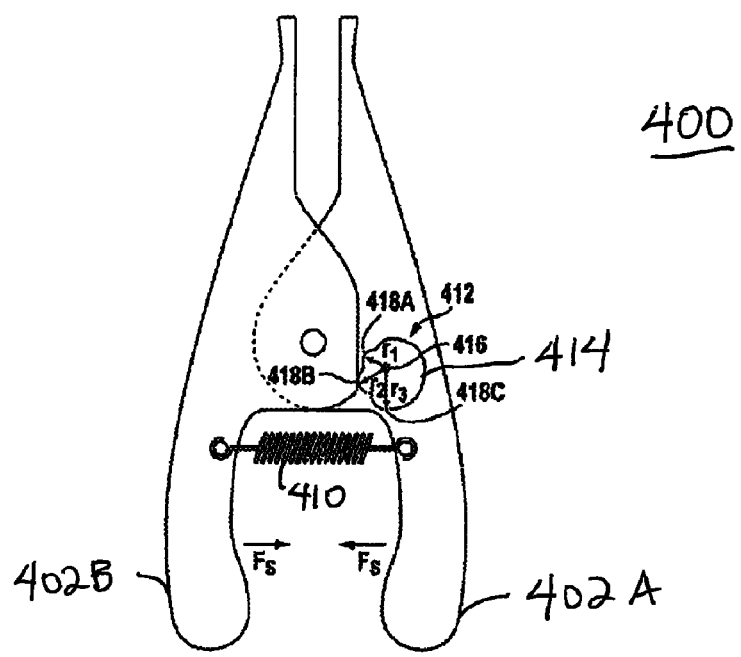

FIG. 8 illustrates a diagram of a tool in accordance with an embodiment. As shown in FIG. 8, the tool 400 is similar in design and operation to the tool 200 described in FIGS. 3A and 3B. In contrast to the tool 200 in FIGS. 3A and 3B, the tool 400 includes an adjustment mechanism 412 having a cam 414 configured to rotate about a cam axle 416 and which includes one or more cam surfaces 418 which bear against the middle body 420 to move the jaws 404A, 404B toward or away from each other a predetermined distance. In particular, the cam 414 shown in FIG. 8 includes three cam surfaces 418A, 418B, and 418C, the cam surfaces having respective radii, $r_1, r_2, r_3$ with respect to the cam axle 416. It should be noted that any number of cam surfaces 418, including just one, is contemplated. In the embodiment shown in FIG. 8, the three radii of the cam surfaces 418A, 418B, and 418C are related as follows: distance of $r_1$ to axle<distance of $r_2$ to axle<distance of $r_3$ to axle. Considering that the spring 410 urges the handles 402A and 404B toward one another, the cam 414 applies a force to the middle body which opposes the spring force $F_S$. Thus, if the cam 414 is actuated such that cam surface 418A having the largest radius, $r_3$, is in contact with the middle body, the cam 414 will force the handles 402A, 402B to move away from one another the greatest distance. This results in the jaws 404A, 404B being moved toward each other. In contrast, as the cam 414 is actuated to a position where the cam surface 418A having the smallest of the available radii, $r_1$, is in contact with the middle body, the cam 414 will force the handles 402A, 402B to move toward one another. This results in the jaws 404A, 404B moving away from one another tool 400, thereby effectively increasing the stiffness in the guidewire 100.

Figure 9:
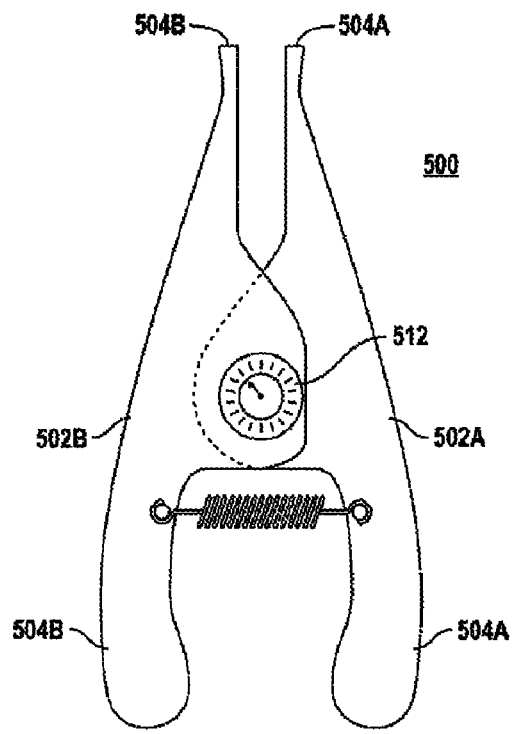

FIG. 9 illustrates a diagram of a tool in accordance with an embodiment. As shown in FIG. 9, the tool 500 is similar in design and operation to the tool 200 described in FIGS. 3A and 3B. In contrast to the tool 200 in FIGS. 3A and 3B, the tool 500 includes an adjustment mechanism 512 having a detent assembly which functions, somewhat analogously to a torque wrench, for allowing the selection of maximum applied tension. The detent setting may be set to a specific force (much like a torque wrench) such that once the designated force to the tool handle exceeds the desired level, the detent mechanism 512 activates and prevents further tensioning of the guidewire. The detent mechanism 512 thus can act as a form of a "safety" against over tensioning the guidewire. As shown in FIG. 10, the tool 500 may include an adjustment mechanism 550 that allows the user to selectively set the stiffness of the guidewire within a particular range (e.g., between the range of 1-6 as shown in FIG. 10).

Figure 11:
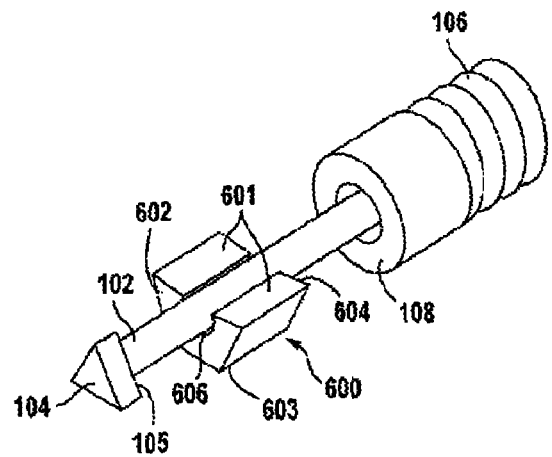
FIG. 11 illustrates a perspective view of a C-shaped guidewire insert in accordance with an embodiment.

FIG. 11 illustrates a perspective view of a guidewire insert or cartridge in accordance with an embodiment. As shown in FIG. 11, the cartridge (also referred to herein as an insert) 600 is positioned between the head 104 and the collar 108 of the guidewire body 106, whereby the cartridge 600 maintains the stiffness in the guidewire 100 by maintaining the head 104 at a desired distance from the collar 108. In particular, the cartridge 600 has a cylindrical body having a proximal end 602 which abuts an inner surface 105 of the guidewire head 104 and a distal end 604 which abuts the guidewire's collar 108. In addition, the cartridge 600 has an inner diameter 606 substantially equal or slightly larger than the diameter of the guidewire's tension wire 102. The cross-section of the cartridge is preferably in the shape of a trapezoid as shown in FIG. 11, although other shapes are contemplated (e.g. C-shaped, square, triangular, etc.) With regard to the embodiment in FIG. 11, the trapezoidal cross-section of the cartridge produces two opposing sides 603 as well as two adjacent faces 601. The opposing sides 603 allow the cartridge to be easily grasped by an engagement tool (discussed below) whereas the adjacent faces 601 allow the cartridge to be easily disengaged by the disengaging tool (discussed below). The adjacent faces 601 preferably encompass 210 degrees of the wire 102, although other angles are contemplated. This configuration (shown in FIGS. 20-22B) allows the disengaging tool to push the faces 601 downward to slightly increase the diameter 606 of the cartridge 600 to disengage the cartridge 600 from the tension wire 102.

The cartridge 600 may be constructed of a durable, rigid, yet slightly flexible material having a high longitudinal compressive strength (e.g. Lexan, Plexiglas, Lucite, Perspex) so that the cartridge 600 can flex open and snap into circumferential position over the core wire 102 and later spring open when it is pushed "away" from the core wire 102 so as to permit removal of the cartridge 600.

It is preferred that the cartridge 600 is smaller than or equal to the diameter of the guidewire's body 106 as well as the cross section of the lumen of the instrument or drug carrying catheters with which the guidewire 100 operates. Accordingly, the cartridge 600 allows the user the freedom to load, unload, advance and retract surgical devices over the proximal end of the guidewire and cartridge 600 while the desired stiffness of the guidewire 100 is maintained without compromising the stiffness of the guidewire 100 and without removing the cartridge 600. Thus, the configuration and dimensions of the cartridge 600 allows the tension of the guidewire 100 to be maintained while the exchange of catheters, balloons, stents and/or other surgical tools and medicine may occur over the guidewire 100 without having to remove the cartridge 600 or exchange guidewires.

Figure 12:
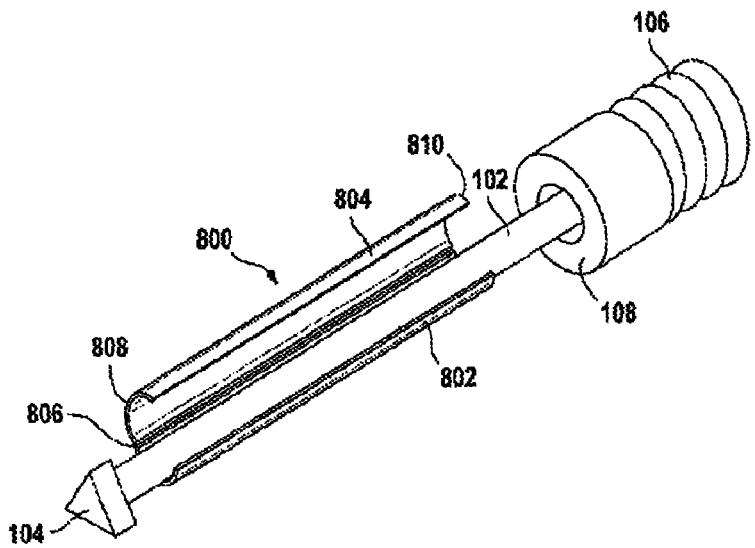
FIG. 12 illustrates a perspective view of a clamshell guidewire insert in accordance with an embodiment.
Figure 13A:
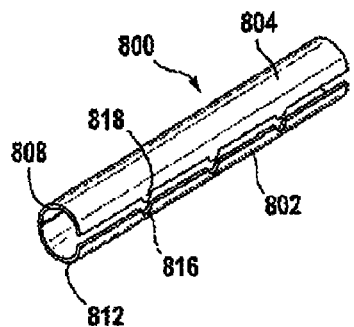
FIGS. 13A-13C illustrate perspective views of a selectively openable guidewire insert in accordance with an embodiment.

FIGS. 12 and 13A-13D illustrate perspective views of a selectively openable guidewire insert 800 in accordance with an embodiment. As shown, the insert 800 is positioned between the head 104 and the collar 108 of the guidewire body 106, whereby the insert 800 maintains the stiffness in the guidewire 100 by maintaining the head 104 at a desired distance (and desired tension) from the collar 108. In particular, the insert 800 has a cylindrical body having a proximal end 808 which abuts the guidewire head 104 and a distal end 810 which abuts the guidewire's collar 108 when the insert 800 is coupled to the tension wire 102. In addition, as shown in FIG. 13A, the insert 800 has an inner diameter 812 as well as an outer diameter 814, whereby the inner diameter 812 is substantially equal or slightly larger than the diameter of the guidewire's tension wire 102. It is preferred that the outer diameter 814 of the insert 800 is smaller than or equal to the diameter of the guidewire's body 106. Further, it is preferred that the overall outer diameter of the insert 800 is smaller in cross section than the lumen of the surgical components with which the guidewire 100 operates. Accordingly, the insert 800 allows the user the freedom to load, unload, advance and retract surgical devices over the proximal end of the guidewire and insert 800 while the desired stiffness of the guidewire 100 is maintained.

As shown in FIG. 12, the insert 800 has a clam-shell configuration having a lower portion 802 and an upper portion 804 coupled to one another at a hinge 806. The hinge 806 may be created as an integral score in the insert's 800 material. This configuration allows the insert 800 to be applied over the extended wire 102 in an open position (as shown in FIG. 12) and then actuated or snapped to a locked position by closing the clam shell configuration around the extended wire 102. The material of the insert 800 is durable and rigid to force the head 104 from the collar 108 and thus maintain stiffness in the guidewire 100.

In operation, after the tool 200 moves the head 104 a desired distance with respect to the collar 108 to achieve the desired amount of stiffness, the clamshell-like insert 800 is applied and secured around the tension wire 102 to maintain the increased guidewire stiffness after the tool 200 is removed. As discussed below, the upper and lower portions of the insert 800 may be completely separated from one another prior to and/or after the insert 800 is coupled to the tension wire 102.

FIG. 13A illustrates the clamshell insert 800 having a snap-fit configuration in which the upper portion 804 includes one or more male protrusions 818 and the lower portion 802 includes one or more female receivers 816 which receive the male protrusions 818 to lock the insert 800 in the closed position. It should be noted that the snap-fit configuration shown in FIG. 13A is an example only and other appropriate locking mechanisms are contemplated. For example, the lower and upper portions 802, 804 may be maintained in the closed position by magnets, screws, etc. In addition, the insert 800 may be made of any appropriate material which maintains the head 104 at the desired distance from the collar 108. For example, the insert 800 may be made of durable plastic, stainless steel, aluminum, composite alloys, etc. Inserts 800 of different length may be provided to sustain various amounts of stiffness in the guidewire 100. In an embodiment, the insert 800 may be stamped to have stiffness information on its outer surface to easily inform the user as to how much tension the guidewire 100 will experience upon the insert 800 being applied thereto. In an embodiment, the insert 800 may be disposable and of one-time use, although the insert 800 may alternatively be reused. It should be noted that the above-described design of the insert 800 facilitates fast, simple placement and removal.

Figure 13B:
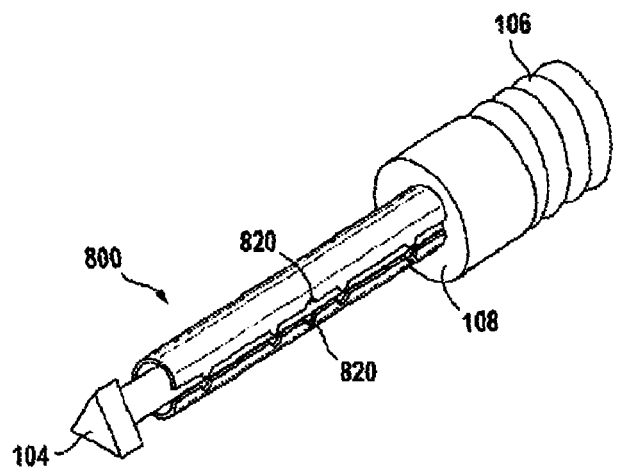
Figure 13C:
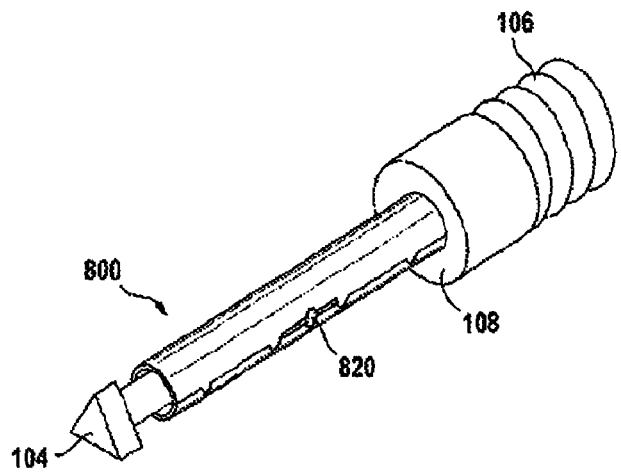

FIG. 13B illustrates an embodiment in that the insert 800 is shown almost closed over the tension wire 102. As shown in FIG. 13B, the insert 800 includes an opening 820 along which extends from one end to the opposite end of the body, whereby the opening remains even after the insert 800 is actuated to the closed position. The opening 820 allows a corresponding tool to remove the insert from the tension wire 104 by pulling the portions adjacent to the opening 820 apart enough to increase the width of the opening 820. Upon width of the opening 820 being large enough, the insert 800 will then be able to be easily removed from tension wire 102. This allows the user to quickly remove the insert 800 to adjust the stiffness of the guidewire 100. It should be noted that the above-described design of the insert 800 facilitates fast, simple placement and removal.

Figure 13D:
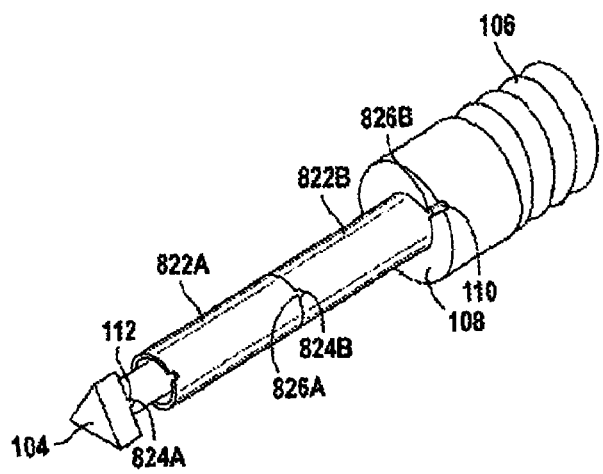
FIG. 13D illustrates a perspective view of a guidewire with combinable cartridges in accordance with an embodiment.

FIG. 13D illustrates a perspective view of a guidewire with combinable cartridges in accordance with an embodiment. As shown in FIG. 13D, the guidewire 100 includes an index groove 110 located on the collar 108. In addition, the tension head 104 is shown to include an index ridge 112, whereby the ridge 112 is configured to fit completely into index groove 110 when the tension head 104 abuts the collar 108 when the guidewire 100 is in a relaxes natural state.

In the embodiment in FIG. 13D, one or more cartridges 822 are shown coupled to the guidewire 100 whereby the cartridges are shown consecutively linked to one another to maintain a specified tension in the guidewire 100. In particular, cartridge to 822A and cartridge 822B are coupled to one another and positioned end to end between the tension head 104 and the collar 108 of the guidewire 100. As shown in FIG. 13D, cartridge 822A includes a cartridge groove or detent 824A on the end proximal to the tension head 104 and a cartridge ridge or protrusion 826A on the opposite end. Similarly, cartridge 822B includes a cartridge groove 824B on the end which abuts the cartridge ridge 826A of cartridge 822A and a cartridge ridge 826B on its opposite end, whereby the cartridge ridge 826B fits within the index groove 110 of the guidewire 100. It should be noted that the index ridge 112 and index groove 110 of the guidewire 100 are not required to utilize the consecutive cartridges having the indexed ridges and grooves. It should also be noted that although two cartridges you shown in FIG. 13D, any number of cartridges may be used with the guidewire. It is also contemplated that any cartridge may have the same features (ridges and/or grooves) on both ends. It should also be noted that the groove and/or ridge features may be applied to any of the other inserts discussed herein and is not limited to only the figures which show them.

Cartridges 822A, 822B each have a length dimension such that the guidewire 100 will undergo a certain amount of stiffness when only one cartridge is used. However, as shown in FIG. 13D, the guidewire 100 will undergo additional stiffness when both cartridges are combined serially and placed over the tension wire 102 of the guidewire 100. This allows the user to variably adjust the amount of stiffness desired on the guidewire 100 by adding or removing cartridges 822 during the procedure. In an embodiment, the cartridges are of equal length, although the cartridges may be of varying lengths in an embodiment. In an embodiment, each cartridge may be marked, or color-coded, with a value which represents the amount of tension which the guidewire 100 would undergo when that particular cartridge is coupled to the guidewire 100. In a further embodiment, these values may be combined to provide a combined tension value which represents the amount of tension which the guidewire 100 would undergo when those combined cartridges are coupled to the guidewire 100. As with the other cartridges described herein, the cartridges in FIG. 13D preferably have an outer diameter smaller than or equal to the outer diameter of the guidewire body 106 to allow ease of loading and unloading of instrument and drug catheters without compromising stiffness in the guidewire 100.

Figure 14:
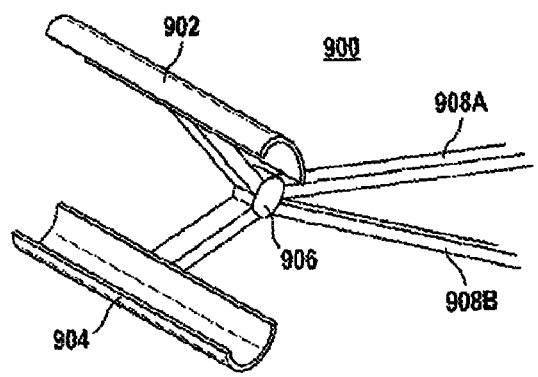
FIG. 14 illustrates a perspective view of an insert placement tool in accordance with an embodiment.

FIG. 14 illustrates a perspective view of an insert placement tool in accordance with an embodiment. As stated above, the upper and lower portions of the insert 800 (FIG. 12) may be completely separated from one another prior to and/or after the insert 800 is coupled to the tension wire 102. In other words, the upper 804 and lower portions 802 of the insert 800 (FIG. 12) may be separate pieces which are not attached at a moveable hinge, but instead include an attachment means which allow the portions 802, 804 to be attached together when coupled to the tension wire 102 and completely disattached from one another when not coupled to the tension wire 102. Such an attachment means may be snap features, magnets, screws, tacks, etc.

In FIG. 14, the insert placement tool 900 is utilized to couple and/or remove the upper and lower portions 804, 802 with respect to the tension wire 102. The tool 900 includes an upper clasp 902 and a lower clasp 904 which are moveable with respect to one another about the joint 906. A pair of handles 908A, 908B are coupled to the joint 906 and are moveable to selectively operate the clasps 902, 904 to move toward and away from one another.

In an embodiment, the claspers 902, 904 have a length dimension which is smaller than the length of the upper and lower portions 802, 804 of the insert 800. This allows the claspers 902, 904 to be placed between the jaws 204A, 204B of the extender tool 200 (FIG. 3A) to deliver the insert 800 to the tension wire 102 while the head 104 is extended away from the guidewire's collar 108. Once the claspers 902, 904 are placed over the tension wire 102, the user preferably actuate the handles 908A, 908B toward one another to couple the upper and lower portions 802, 804 of the cartridge 800 to one another and around the tension wire 102. The insertion tool 900 thereby "snaps" the insert 800 over the tension wire 102 and the tool 900 is then removed from between the tool's jaws. In an embodiment, the claspers 902, 904 do not deliver the insert 800, but instead are themselves placed between the tension head 104 and the collar 108 to maintain the stiffness of the guidewire after the tool 200 is removed.

Figure 15:
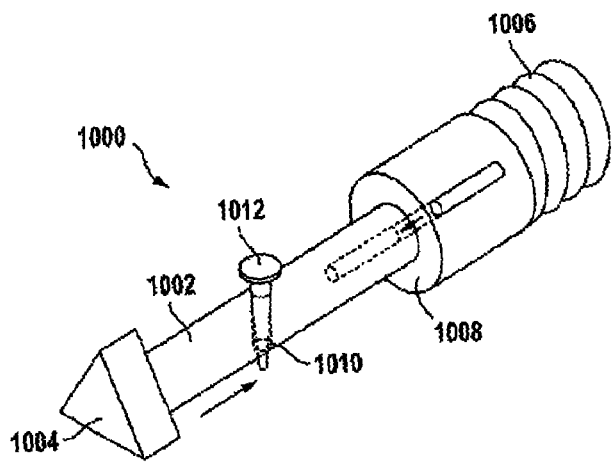
FIG. 15 illustrates a perspective view of self-maintaining guidewire in accordance with an embodiment.

FIG. 15 illustrates a perspective view of self-maintaining guidewire 1000 in accordance with an embodiment. As shown in FIG. 15, the guidewire 1000 includes an aperture 1010 (shown in phantom lines) through the tension wire 1002. Although only one aperture 1010 is shown in FIG. 15, any number of apertures 1010 may be configured along the tension wire 1002. The aperture 1010 is configured to receive a setting pin 1012 therethrough, whereby the guidewire 1000 is able to maintain the desired stiffness when the setting pin 1012, inserted in the desired aperture 1010, abuts the collar 1008. It is preferred that apertures 1010 are configured in a spaced fashion such that the pin 1012 may be inserted into any of the available apertures 1010 which correspond to the desired stiffness which the user wants the guidewire 1000 to achieve.

Figure 16:
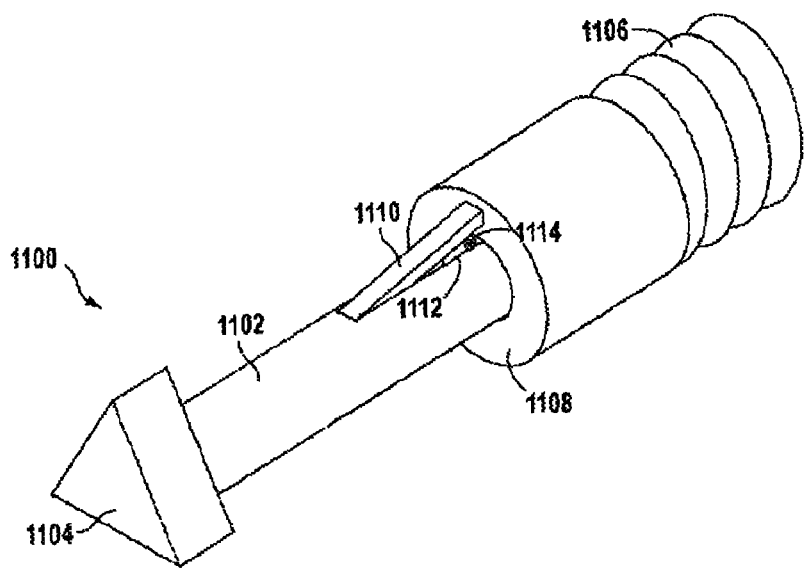
FIG. 16 illustrates a perspective view of self-maintaining guidewire in accordance with an embodiment.

FIG. 16 illustrates a perspective view of self-maintaining guidewire 1100 in accordance with an embodiment. As shown in FIG. 16, the guidewire 1100 includes a foot 1110 which is configured within a corresponding recess 1112 within the tension wire 100. The foot 1110 is preferably urged upward away from the wire 1102 by a spring 1114, such that the foot 1110 "pops out" when it is extended out from within the body 1106 past the collar 1108. In operation, once the tension wire 1102 is extended far enough from the guidewire body 1106, the foot 1100 springs out from the recess 1112 and abuts the collar 1108 to maintain the position and tension of the guidewire 1100. In an embodiment, the tension wire 1102 can be retracted and the guidewire relaxed by pressing the foot 1100 back into the recess 1112 using a tool (e.g. hemostat) and allowing the tension head 1104 to retreat back toward the default position.

Figure 17A:
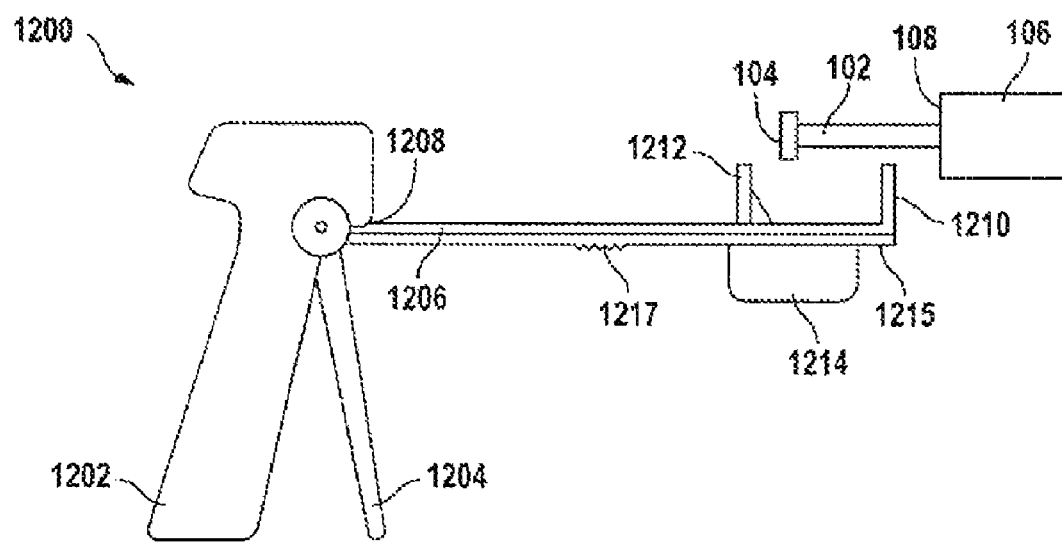
FIG. 17A illustrates a side view of a combined tensioning and insert applicator deployment tool in accordance with an embodiment.

FIG. 17A illustrates a side view of a combined tensioning and insert applicator tool in accordance with an embodiment. In particular, the tool 1200 includes a handle member 1202, a trigger member 1204, an elongated tray 1206, a collar interface 1210, and a tension brace 1212. In an embodiment, the handle member 1202 is designed to have a pistol grip and an elongated trigger member as shown in FIG. 17A, however any other appropriate shape for the handle 1202 and trigger member 1204 is contemplated.

Figure 18:
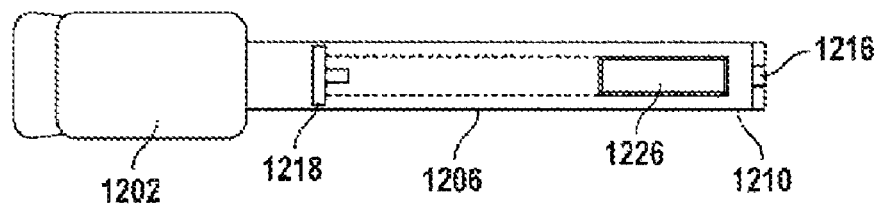
FIG. 18 illustrates a top view of the combined tensioning and insert applicator deployment tool in accordance with an embodiment.

A proximal end 1208 of the elongated tray 1206 is mechanically and operably coupled to the handle 1202 and the trigger 1204. The distal end of the tray 1206 terminates with a collar interface 1210 which is configured to abut the collar 108 of the guidewire body 106 when the tool 1200 is in operation. The collar interface 1210 preferably includes a notch 1216 (FIG. 18) through which the tension wire 102 passes while the tool 1200 is operating with the guidewire 100. The elongated tray 1206 in the embodiment shown in FIG. 17A has an open top in which the tension brace 1212 is exposed. This embodiment allows the user to view the tensioning of the guidewire and as well as movement of the tension brace 1212 along the elongated tray 1206.

Figure 17B:
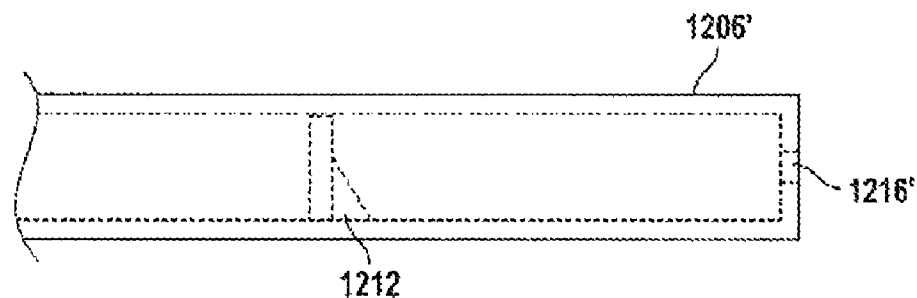
FIG. 17B illustrates an elongated barrel tray in accordance with an embodiment.

In contrast, FIG. 17B illustrates an elongated barrel tray 1206' which it is closed, whereby the interior of the tray cannot be viewed by the user 1206'. As shown in FIG. 17B, the barrel tray 1206' has a notch feature 1216', preferably triangular in cross-section, on its distal end which receives the tension wire as well as the tension head and through which the tension wire 102 passes while the tool is operating with the guidewire 100.

The tool 1200 shown in the embodiment in FIG. 17A also includes a tension brace 1212 which is adjustably moveable along the elongated tray 1206 between the tray's 1206 proximal and distal ends 1208, 1210. In particular, the tension brace 1212 is configured to retract toward the proximal end 1208 as the trigger 1204 is squeezed. In an embodiment, the tension brace 1212 freely moves along the tray 1206 in response to actuation of the trigger 1204. In an embodiment, the tension brace 1212 is urged toward the distal end 1210 by spring 1215. In this embodiment, a rod 1217 is coupled at one end to a rotating cam of the trigger 1204 and another end is coupled to the brace 1212, whereby actuation of the trigger 1204 overcomes the forces on the tension brace 1212 by the spring 1215 to move the tension brace 1212 toward the proximal end 1208.

In an embodiment, the notch feature 1216 is configured to receive a portion of the tension wire 102 therethrough along with the tension head 104 when the tension brace 1212. The tension brace 1212 is preferably positioned proximal to the collar rest 1210 and has a tension head 104 engaging aperture. In an embodiment, the tension brace 1212 has the head engaging aperture as described above in FIGS. 5A-5C or 6A-6C, and the details of the engaging apertures are not discussed again herein. It should be noted that other configurations of head engaging apertures are contemplated.

Figure 19:
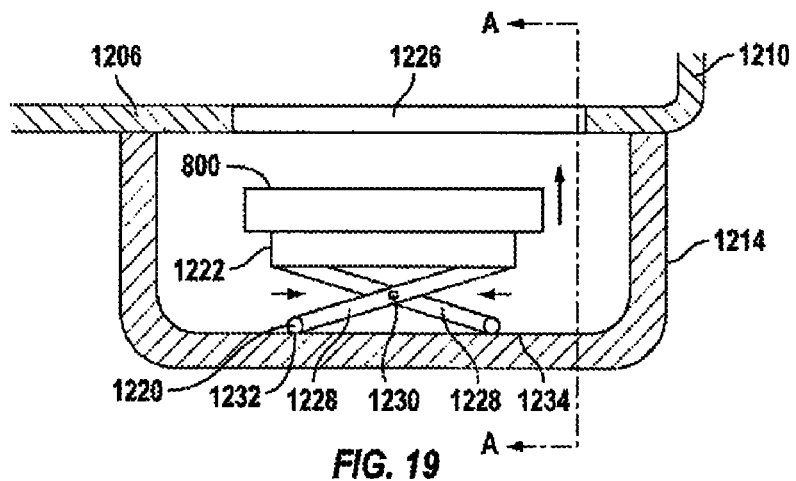
FIG. 19 illustrates a broken view of a magazine for use in a deployment tool in accordance with an embodiment.
Figure 20:
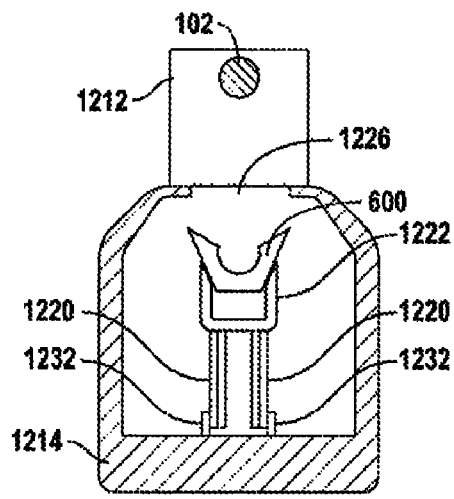
FIGS. 20 and 21 illustrate operation of the magazine with the deployment tool in accordance with an embodiment.

In the embodiment in FIG. 17A, the tool 1200 includes a magazine 1214 configured to house one or more of the cartridge inserts described above. The magazine 1214 is shown preferably coupled to and positioned below the elongated tray 1206, although it is contemplated that the magazine may be positioned above or to the side of the elongated tray 1206. FIG. 20 illustrates an broken view of an interior of the cartridge magazine 1214 in accordance with an embodiment. In general, the cartridge magazine 1214 preferably houses the cartridge prior to coupling the cartridge to the tension wire 102 of the guidewire 100. In an embodiment, the cartridge magazine 1214 additionally or alternately retrieves and stores the cartridge after the cartridge has been coupled to the tension wire 102. As shown in FIG. 19, the magazine 1214 preferably includes a lifter mechanism 1220 positioned within the magazine 1214 along with a cartridge inserter 1222 which is coupled to the lifter mechanism 1220.

Figure 21:
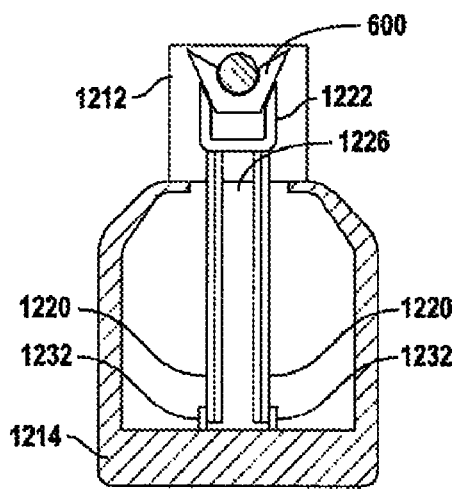

As shown in FIGS. 19-21, the lifter mechanism 1220 preferably comprises one or more sets of scissor members 1228 which are coupled to one another about an axis, whereby each scissor member 1228 includes a roller 1232 on its end. The scissor members 1228 preferably move along a receiving groove along the bottom surface 1234 of the magazine 1214 such that the rollers 1232 move along only one dimension within the magazine 1214. Alternatively, the scissor members 1228 move along a smooth surface within the bottom surface 1234 of the magazine 1214. In operation, the rollers 1232 move along the bottom surface 1234 toward one another to cause the lifter mechanism to move upward toward the tray 1206. In an embodiment, the lifter mechanism 1220 preferably urges the cartridge inserter 1222 to move in an upward direction by the use of a spring. In another embodiment, a separate actuating control (not shown) external to the magazine 1214 is used to selectively cause the lifter mechanism 1220 to move upward and/or downward with respect to the tray 1206. Such an actuating control may be a mechanical and/or electronic switch, lever, button or other actuating means. In an embodiment, the magazine 1214 is capable of easily being disengaged from the tool 1200. This allows the magazine 1214 to be reloaded with one or more cartridges, or be replaced with an already full magazine which is then coupled to the tool 1200.

As shown in FIGS. 20 and 21, the cartridge inserter 1222 has a U-shaped configuration, whereby angled ends of the inserter 1222 preferably come into contact the sides 603 of the cartridge 600 (See FIG. 11) and allow the inserter 1222 to securely hold and move the cartridge 600 to engage the wire 102. The magazine 1214 is preferably positioned underneath the elongated tray 1206, whereby the tray 1206 includes an aperture 1226 in communication with the interior of the magazine 1214 as shown in FIG. 20. In an embodiment, the aperture 1226 has a length dimension along the elongated tray 1206 to allow specific sized cartridges to pass therethrough. In an embodiment, the aperture 1226 has a length dimension which traverses the entire length of the elongated tray 1206 to allow any sized cartridges to pass therethrough. The aperture 1226 allows the cartridge 800 to be deployed within the magazine in an upward direction to come in contact with and couple to the tension wire 102 as the tension wire 102 is extended by the tension brace 1212. In an embodiment, the aperture 1226 constantly remains open in the elongated tray 1206. In an embodiment, the aperture 1226 has a door which selectively opens to allow the cartridge to be deployed around the tension wire 102.

In operation, as shown in FIG. 20, the user operates the tool 1200 by placing the collar rest 1210 against the collar 108 of the guidewire 100. The tensioning head 104 is inserted through the notch feature 1216 and is then engaged and locked with the tension brace 1212. The tension brace 1212 may have any of the engaging apertures described above. The user then gradually applies force to the trigger 1204 to cause the tension brace 1212 to gradually move from the collar rest 1210 toward the handle 1202. As the tension brace 1212 moves toward the proximal end of the tray 1206 the tensioning wire 102 extends and thus causes the guidewire to increase in stiffness. Once the tension brace 1212 moves away from the aperture 1226 a desired distance, the lifter mechanism 1220 preferably automatically actuates to cause the scissor members 1228 to move toward one another and cause the cartridge holder 1222 as well as a cartridge 600 to move upward through the aperture 1226 and around the tension wire 102. In an embodiment, the user operates a separate actuator mechanism to cause the lifter mechanism 1220 to operate. Preferably, the quick upward movement of the inserter 1222 and cartridge 600 causes the cartridge 600 to snap around the tension wire 102, as shown in FIG. 21.

As stated above, the cartridge 600, once deployed, will maintain the tension of the guidewire. This allows the user to depress the trigger, which causes the tension brace 1212 to move back toward the distal end of the elongated tray 1206 and abut the end of the cartridge 600. The tension head 104 is then disengaged from the tension brace 1212. The tool 1200 is then preferably removed from the guidewire 100 to allow surgical tools and/or drugs to be delivered along the tensioned guidewire via the guidewire's proximal end.

Figure 22A:
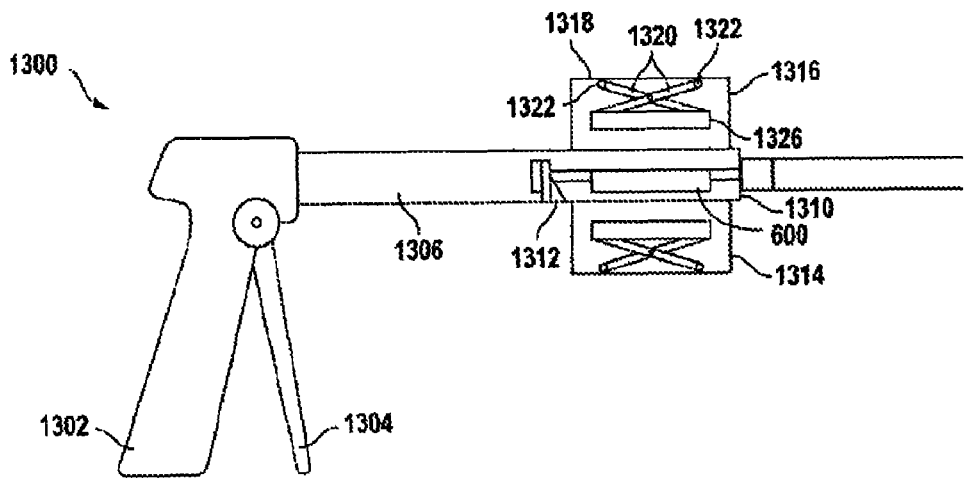
FIG. 22A illustrates a side view of a combined tensioning as well as an cartridge applicator and removal tool in accordance with an embodiment.

FIG. 22A illustrates a side view of a combined tensioning as well as an cartridge applicator and removal tool in accordance with an embodiment. As with the tool discussed in FIGS. 17-21, the tool 1300 includes a handle member 1302, a trigger member 1304, a closed, barrel-shaped elongated tray 1306, a collar interface 1310, and a tension brace 1312. As with the embodiment in FIG. 17A, the handle member 1302 is designed to have a pistol grip and an elongated trigger member 1304, although any other appropriate shape for the handle 1302 and trigger member 1304 is contemplated.

As with the embodiment in FIG. 17A, the tool 1300 includes a magazine 1314 positioned below the barrel tray 1306 and is configured to deploy a cartridge around the tension wire 102 of the guidewire 100 when the tension head 104 is extended a desired distance from the collar interface 1310. As with the embodiment in FIG. 17A, the barrel tray 1306 may include an aperture in its bottom surface which is in communication with the interior of the magazine 1314. As stated above, the magazine 1314, upon actuation, moves the cartridge 600 upwards through the aperture in the bottom surface of the barrel tray 1306. Upon the cartridge 600 coming in contact with the tension wire 102, the cartridge 600 couples to the tension wire 102 to prevent the tension wire 102 from reverting back to the collar 108 or the relaxed default position of the guidewire 100.

In the embodiment in FIG. 22A, the tool 1300 also includes a removal magazine 1316 preferably positioned above the barrel tray 1306. The removal magazine 1316 houses a removal mechanism that is configured to remove an already deployed cartridge 600 from the tension wire 102 when the cartridge 600 is no longer needed. In an embodiment, the removal magazine 1316 is in communication with an aperture in the top surface of the barrel tray 1306 to allow the cartridge 600 to be removed from the tray 1306 and moved into the removal magazine 1316.

In the embodiment in FIG. 22A, the lifter mechanism 1318 preferably comprises one or more sets of scissor members 1320 which are coupled to one another about an axis. In an embodiment, each scissor member 1320 includes a roller 1322 on its end. The scissor members 1320 preferably move along a receiving groove along the top surface 1324 of the magazine 1316 such that the rollers 1322 move along only one dimension within the magazine 1316. Alternatively, the scissor members 1320 move along a smooth surface of the top surface 1324 of the magazine 1316. In operation, the rollers 1322 move toward one another to cause the lifter mechanism to move downward toward the barrel tray 1306. In an embodiment, the removal mechanism 1318 preferably urges the cartridge remover 1326 to move in a downward direction via a spring. In another embodiment, a separate actuating control (not shown) external to the magazine 1316 is used to selectively operate the removal mechanism 1318 when the user desires. Such an actuating control may be a mechanical and/or electronic switch, lever, button or other actuating means.

Figure 22B:
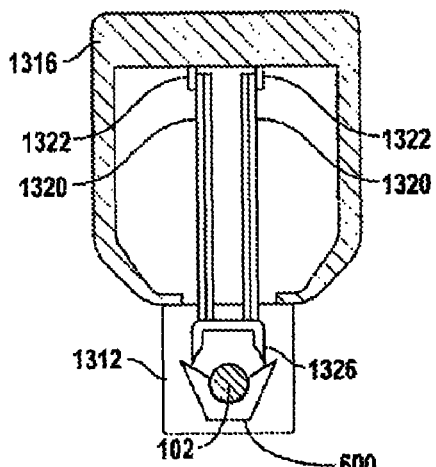
FIG. 22B illustrates operation of the magazine with the removal tool in accordance with an embodiment.

FIG. 22B illustrates an end view of the tool 1300 with removal mechanism 1318 in accordance with an embodiment. The insert magazine 1314 is not shown in FIG. 22B for clarity purposes. In an embodiment, the cartridge remover 1326 has a similar cross-sectional shape to the inserter 1222 shown in FIGS. 20 and 21 in which the remover 1326 has a U-shaped configuration with angled ends. The ends of the remover 1326 come into contact with the slightly angled faces 601 of cartridge 600, whereby the pointed ends press against the faces 601, as shown in FIG. 22B. As the ends of the remover 1326 press against the faces 601, the forces cause the faces 601 to the bend downward and outward with respect to the aperture 606. Upon sufficient force being applied to the faces 601, the movement of the faces 601 away from one another causes the diameter of the aperture 606 to slightly increase, thereby allowing the cartridge 600 to slip off of the tension wire 102, thereby disengaging the cartridge 600 from the wire 102.

It should be noted that although an example is shown and described as to the construction of the removal mechanism, any appropriate construction which allows the cartridge remover 1326 to move to the barrel tray 1306 and remove the cartridge 800 is contemplated. It should be noted that although the figure shows two separate magazines, one for insertion and one for removal of the cartridge, is contemplated that one magazine may be used to perform both insertion and removal functions in an embodiment. It should also be noted that although the cartridge 600 is discussed in relation with the embodiments in FIGS. 19-22B, any other shaped cartridge may be used as a substitute with appropriately modified inserter and/or remover devices.

In an embodiment, the magazine 1318 is capable of easily being disengaged from the tool 1300. This allows one or more cartridges collected by the magazine to be unloaded from the tool 1300. In an embodiment, the detaching feature allows a magazine full of used cartridges to be replaced with an empty removal magazine for continuing use. In an embodiment, the removal magazine 1318 includes one or more windows (not shown) to allow the user to view inside the magazine 1318 and see the collected cartridges or an aperture for the ejection of spent or used cartridges.

Figure 23A:
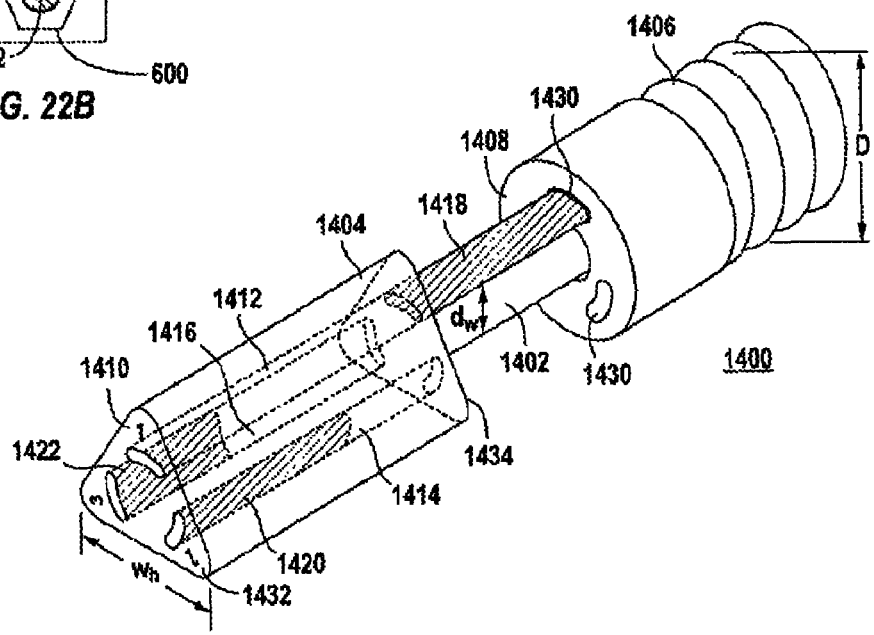
FIG. 23A illustrates a perspective view of a guidewire with integrated tension head and tension maintaining mechanism in accordance with an embodiment.

FIG. 23A illustrates a perspective view of a guidewire with integrated tension maintaining mechanism in accordance with an embodiment. As shown in FIG. 23A, the guidewire 1400 preferably includes a body 1406 having a tension wire 1402 and a tension head 1404 coupled to a proximal end of the tension wire 1402.

The body 1406 has a diameter D, whereby the tension wire 1402 has a diameter $d_w$, and the tension head 1404 has a width dimension $w_h$. The diameter $d_w$ of the tension wire 1402 is preferably smaller than the diameter D of the body 1406. Additionally, it is preferred that the width $w_h$ of the tension head 1404 is greater than the diameter $d_w$ of the tension wire 1402 but preferably smaller than the diameter D of the body 1406. The smaller width dimension $w_h$ of the tension head 1404 allows the user to load and unload other surgical tools via the head 1404 and onto the coil body 1406 while simultaneously maintaining the desired stiffness of the guidewire 1400.

The tension head 1404 has an integrated tension maintaining mechanism 1410 in which the mechanism 1410 includes one or more channels which are configured to house tensioning legs, as shown in FIG. 23A. In the embodiment shown in FIG. 23A, the tension maintaining mechanism 1410 includes channels 1412, 1414 and 1416, each preferably located near the angles of the triangular head 1404, although placement of the channels can be anywhere on the head 1404. In an embodiment, the channels 1412, 1414 and 1416 extend entirely through the tension head, whereby one or more of the channels 1412, 1414 and 1416 have an aperture in surface 1432 and opposing surface 1434. In an embodiment, the channels 1412, 1414 and 1416 only extend out of surface 1434 of the tension head 1404.

The channels 1412, 1414 and 1416 preferably house respective tension legs 1418, 1420, 1422 which are slidably moveable in and out of the channels in a linear direction. Each tension leg has a proximal end which preferably remains attached to the tension head 1404 and a distal end which comes in contact and abuts the collar 1408 of the guidewire 1400. When in the retracted mode, as with legs 1420, 1422 in FIG. 23A, the legs 1420, 1422 remain within their respective channels 1420, 1422 and preferably do not come into contact with the collar 1408. In contrast, when the leg is in the extended mode, as with tension leg 1418, the leg 1418 abuts the collar 1408 and forces the tension head 1404 to remain positioned away from the collar 1408 to ensure that the guidewire maintains its desired stiffness. In an embodiment, it is contemplated that the collar 1408 may include one or more detents 1430 which are configured to receive the distal end of the respective tension leg. The detents 1430 aid in stabilizing the tension leg in the extended position and prevent the tension leg from slipping off the surface of the collar 1408.

In an embodiment in which the mechanism 1410 utilizes more than one tension leg, it is preferred that the tension legs have different length dimensions, although this is optional. As shown in FIG. 23A, tension leg 1420 has a greater length dimension compared to leg 1422, but a smaller length dimension than leg 1418. Considering that the stiffness of the guidewire 1400 is directly proportional to the distance between the tension head 1404 and the collar 1408, the guidewire 1400 will experience greater stiffness when tension leg 1418 is in the extended position than when tension leg 1420 is in the extended position. In comparison, the guidewire 1400 will experience less stiffness when tension leg 1422 is in the extended position than when tension leg 1420 is in the extended position. This allows the user to selectively choose which tension leg to utilize based on the desired stiffness of the guidewire 1400.

The tension legs 1418, 1420, 1422 are preferably attached to the channels at their proximal ends to prevent the legs 1418, 1420, 1422 from becoming disengaged from the tension head 1404. The mechanism 1410 is configured to ensure that the extended tension leg is able to withstand the forces which urge the tension head 1404 to move toward the collar 1408. In an embodiment, a spring (not shown) within the tension head 1404 urges the tension leg to the extended position, whereby the spring is rated with a constant k such that the spring force will be higher than any opposite force that urges head 1404 and collar 1408 toward one another.

Figure 23B:
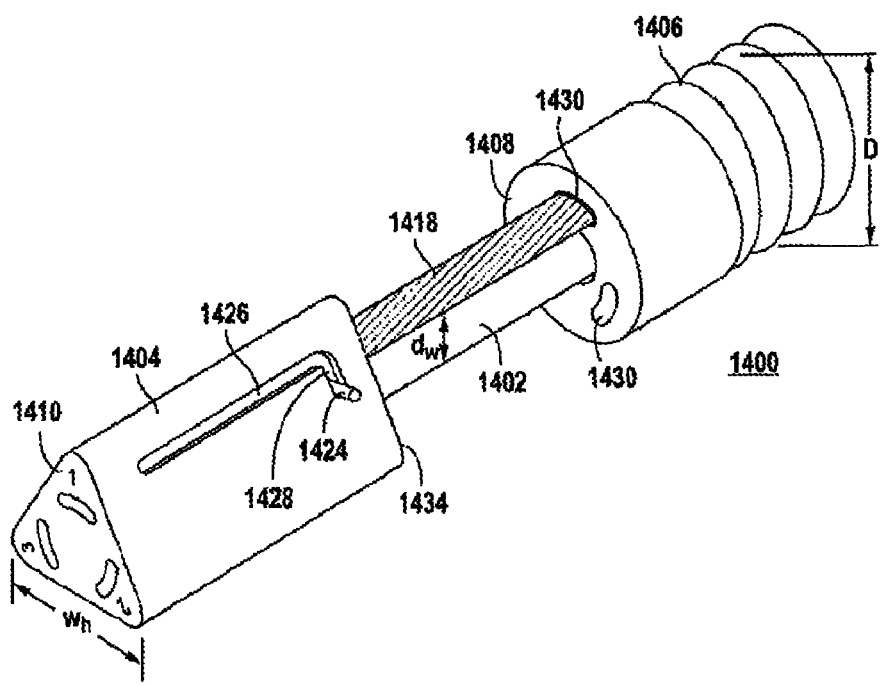
FIG. 23B illustrates a perspective view of a guidewire with integrated tension head and tension maintaining mechanism in accordance with an embodiment.

In an embodiment, FIG. 23B, an actuator 1424 which is attached to leg 1418 protrudes out of an elongated aperture 1426 in the tension head 1404, whereby the user can slidably move the actuator 1424 along an elongated aperture 1426 to slide the leg 1418 in or out of the head 1404. As shown in FIG. 23B, the elongated aperture 1426 includes a stop detent 1428 in which the actuator 1424 may be set to ensure that the leg 1418 remains in the extended position to maintain the stiffness in the guidewire 1400. In the example shown in FIG. 23B, the stop detent 1428 is positioned at the end of the window 1426 closest to the tension wire 1402, although one or more intermediate stop detents may be configured at desired locations along the elongated aperture 1426 to allow the user to achieve various intermediate lengths of the tension leg (and associated stiffness from the guidewire) by locking the actuator 1424 in any of the desired intermediate detents.

In an embodiment, the tension head 1404 is configured to be rotatable about an axis oriented along the length of the tension wire 1402. This would allow the user to simply rotate the tension head 1404 to a desired position which may be less cumbersome for the user to extend or retract a tension leg based on the orientation of the guidewire 1400 during a procedure. Alternatively, the tension head 1404 is not rotatable about the tension wire 1402 and is fixedly coupled thereto.

Figure 24:
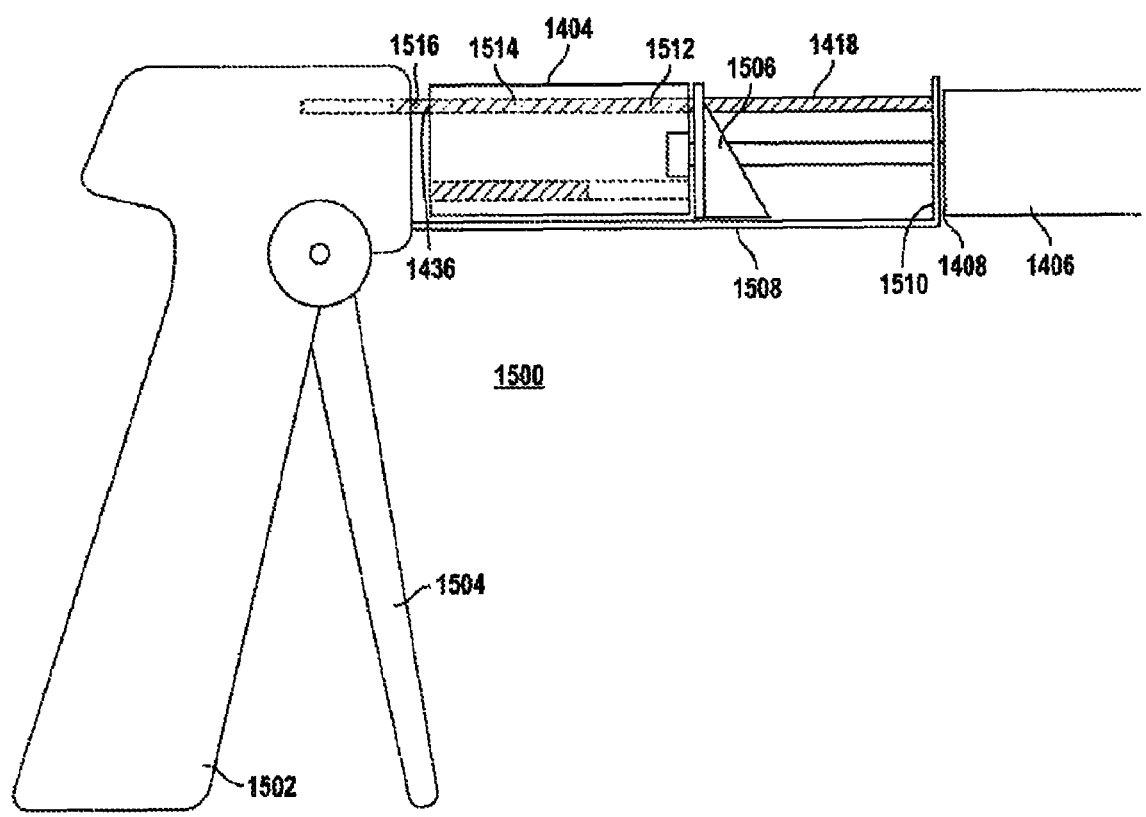
FIG. 24 illustrates a side view of the integrated guidewire tension maintaining head with a deployment tool in accordance with such an embodiment.

In an embodiment, the integrated guidewire tension maintaining head may be combined with a tool to actuate the tension legs. FIG. 24 illustrates a side view of the integrated guidewire tension maintaining head 1400 with deployment tool 1500 in accordance with such an embodiment. The deployment tool 1500 preferably includes a handle member 1502, a trigger member 1504, an elongated tray 1508, a tension brace 1506, and a collar interface 1510. Although the handle member 1502 is shown to have a pistol grip and an elongated trigger member 1504, other appropriate shapes for the handle 1502 and/or trigger member 1504 are contemplated.

As shown in FIG. 24, the tension head 1404 is positioned within the deployment tool 1500 between the handle 1502 and the tension brace 1506. The handle 1502 preferably includes an actuating pin 1512 positioned within a chamber 1514 therein, whereby the pin 1512 preferably extends out of the handle 1502 when the trigger 1504 is depressed. The tool 1500 preferably includes an aperture 1516 on the handle 1502 which is in communication with the pin chamber 1514. In an embodiment, the aperture 1516 is aligned with a receiving aperture 1436 of the tension head 1404 such that the pin 1512, upon being actuated, extends out of the chamber 1514 passes through aperture 1436 to press the tension leg 1418 out of channel 1412. As stated above, the tension leg 1418 extends out of head 1404 to the extended position in which the leg 1418 abuts the collar 1408.

In the embodiment in FIG. 24, the tension leg 1418 separates the distance between the tension head 1404 and the collar 1408. It is contemplated that the tension brace 1506 may aid in separating the tension head 1404 from the collar 1408 in that a combination of the tension brace 1506 and tension leg 1418 maintain stiffness of the guidewire. The tension brace 1506 preferably includes an aperture which is aligned with the exit aperture 1438 of the tension head 1404 such that the tension leg 1418 passes through the tension brace 1506 and abuts the collar interface 1510.

As stated, the tension head 1404 is rigidly attached to the tension wire 1402 and guidewire body 1406. In an embodiment, the tension head 1404 is rigidly attached to the deployment tool 1500. In an embodiment, the tension head 1404 is not rigidly attached to the deployment tool 1500, whereby the deployment tool 1500 may be used with different classes of guidewires having differently dimensioned tension heads and/or tension legs.

It should be noted that the tension head 1404 is shown in FIGS. 23 and 24 have a triangular shape. Although this is a preferred shape, the tension head 1404 may alternatively have any other shape including, but not limited to, square, hexagonal, pentagonal, trapezoidal, spherical, circular, etc. It should be noted that the tension legs are shown in the Figures as bean-shaped, the tension legs may have any cross sectional shape, such as square, circular, rectangular, etc. Although three channels and tension legs are described above, it should be noted that any number of channels and tension legs, such as one channel or leg, are contemplated for a particular tension head.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

We claim:

1. A variable-stiffness guidewire system comprising:
an elongated flexible guidewire, the guidewire having a body and a guidewire head coupled to the body, the guidewire including a guidewire collar proximal to the guidewire head, the guidewire head slidably moveable with respect to the guidewire collar via a tensioning wire to adjust a stiffness of the guidewire; and
a tool configured to engage the guidewire head and move the guidewire head a desired distance from the guidewire collar to achieve a desired stiffness, the tool having a first mechanism configured to selectively attach an insert to the guidewire between the guidewire head and the guidewire collar, wherein the insert maintains the desired stiffness of the guidewire
wherein the guidewire head is triangular in shape, the tool further comprises an engaging mechanism configured to engage the guidewire head, the engaging mechanism including:
a first triangular-shaped engaging aperture extending from a first surface to a second surface of the tension brace, the first aperture positioned in a first orientation to allow the triangular guidewire head to pass from the first surface to the second surface when the triangular guidewire head is aligned with the first orientation of the first engaging aperture; and
a second triangular-shaped engaging aperture extending from the second surface only partially toward the first surface of the tension brace, the second aperture positioned in a second orientation at an angle with respect to the first orientation of the first aperture, wherein the second aperture is configured to engage the triangular guidewire head when the triangular guidewire head is aligned with the second orientation of the first engaging aperture.

2. The system of claim 1, wherein the insert remains between the guidewire head and the guidewire collar and maintains stiffness of the guidewire after the tool disengages the guidewire.

3. The system of claim 1, wherein the tool further comprises:
a second mechanism coupled to the tool, the second mechanism configured to selectively remove the insert from between the guidewire head and the guidewire collar.

4. The system of claim 1, wherein the insert has a cross-sectional dimension smaller than a diameter of the body of the guidewire.

5. The system of claim 1, wherein the insert has a cross-sectional dimension substantially equal to a diameter of the body of the guidewire.

6. The system of claim 1, wherein the tool further comprises an engaging mechanism including a tension brace and a collar interface, the tension brace configured to engage the guidewire head and the collar interface configured to abut the guidewire collar, the tension brace actuatable between a retracted position and an extended position with respect to the collar interface, wherein the insert is positioned between the guidewire head and the guidewire collar when the tension brace is in the extended position.

7. A tool for use with a variable-stiffness guidewire having a guidewire head and a guidewire collar, the tool comprising:
a body;
an engaging mechanism coupled to the body and adapted to engage a guidewire head of a guidewire;
an actuator coupled to body and configured to move the engaging mechanism and the guidewire head away from a guidewire collar a first distance to achieve a first stiffness of at least a portion of the guidewire; and
a mechanism coupled to the body and configured to selectively remove an insert coupled to the guidewire, the insert having a length dimension substantially equal to the first distance positioned between the guidewire head and the guidewire collar to maintain the first stiffness in the at least a portion of the guidewire
wherein the guidewire head is triangular in shape, the engaging mechanism further comprising:
a first triangular-shaped engaging aperture extending from a first surface to a second surface of the tension brace, the first aperture positioned in a first orientation to allow the triangular guidewire head to pass from the first surface to the second surface when the triangular guidewire head is aligned with the first orientation of the first engaging aperture; and
a second triangular-shaped engaging aperture extending from the second surface only partially toward the first surface of the tension brace, the second aperture positioned in a second orientation at an angle with respect to the first orientation of the first aperture, wherein the second aperture is configured to engage the triangular guidewire head when the triangular guidewire head is aligned with the second orientation of the first engaging aperture.

8. The tool of claim 7, further comprising an insert mechanism configured to selectively attach the insert between the guidewire head and the guidewire collar to achieve the first stiffness.

9. The tool of claim 7, wherein the engaging mechanism is configured to move the guidewire head back toward the guidewire collar after the insert is removed to decrease the first stiffness of the guidewire.

10. The tool of claim 8, wherein the engaging mechanism is configured to move the guidewire a second distance with respect to the guidewire collar after the insert is removed to achieve a second stiffness in the guidewire, wherein the insert mechanism is configured to selectively deploy a second insert having a length dimension substantially equal to the second distance to maintain the second stiffness.

11. The tool of claim 7, wherein the engaging mechanism further comprises a tension brace and a collar interface, the tension brace configured to engage the guidewire head and the collar interface configured to abut the guidewire collar, the tension brace actuatable between a retracted position and an extended position with respect to the collar interface, wherein the insert is removed from between the guidewire head and the guidewire collar when the tension brace is in the extended position.

12. The tool of claim 7, wherein the mechanism itself is selectively removeable from the body of the tool.

13. A tool for use with a variable-stiffness guidewire having a guidewire head and a guidewire collar, the tool comprising:
   a body;
   an engaging mechanism coupled to the body and adapted to engage a guidewire head of a guidewire;
   an actuator coupled to body and configured to move the engaging mechanism and the guidewire head away from a guidewire collar a first distance to achieve a first stiffness of at least a portion of the guidewire; and
   a mechanism coupled to the body and configured to selectively attach an insert to the guidewire between the guidewire head and the guidewire collar, the insert having a length dimension substantially equal to the first distance between the guidewire head and the guidewire collar, wherein the insert maintains the first stiffness in at least a portion of the guidewire
   wherein the guidewire head is triangular in shape, the engaging mechanism further comprising:
      a first triangular-shaped engaging aperture extending from a first surface to a second surface of the tension brace, the first aperture positioned in a first orientation to allow the triangular guidewire head to pass from the first surface to the second surface when the triangular guidewire head is aligned with the first orientation of the first engaging aperture; and
      a second triangular-shaped engaging aperture extending from the second surface only partially toward the first surface of the tension brace, the second aperture positioned in a second orientation at an angle with respect to the first orientation of the first aperture, wherein the second aperture is configured to engage the triangular guidewire head when the triangular guidewire head is aligned with the second orientation of the first engaging aperture.

14. The tool of claim 13, further comprising a removal mechanism configured to selectively remove the insert positioned between the guidewire head and the guidewire collar.

15. The tool of claim 14, wherein the engaging mechanism is configured to move the guidewire head back toward the guidewire collar after the insert is removed to decrease stiffness in the guidewire.

16. The tool of claim 14, wherein the engaging mechanism is configured to move the guidewire a second distance with respect to the guidewire collar after the insert is removed to achieve a second stiffness, wherein the mechanism is configured to selectively deploy a second insert having a length dimension substantially equal to the second distance between the guidewire head and the guidewire collar to maintain the second stiffness of the guidewire.

17. The tool of claim 13, wherein the engaging mechanism including a tension brace and a collar interface, the tension brace configured to engage the guidewire head and the collar interface configured to abut the guidewire collar, the tension brace actuatable between a retracted position and an extended position with respect to the collar interface, wherein the insert is positioned between the guidewire head and the guidewire collar when the tension brace is in the extended position.

* * * * *